(12) United States Patent
Fukui et al.

(10) Patent No.: US 10,538,791 B2
(45) Date of Patent: Jan. 21, 2020

(54) METHOD FOR PRODUCING POLYHYDROXYALKANOATE COPOLYMER FROM SACCHARIDE RAW MATERIAL

(71) Applicants: Tokyo Institute of Technology, Meguro-ku, Tokyo (JP); Kaneka Corporation, Osaka-shi, Osaka (JP)

(72) Inventors: Toshiaki Fukui, Tokyo (JP); Izumi Orita, Tokyo (JP)

(73) Assignees: Tokyo Institute of Technology, Tokyo (JP); Kaneka Corporation, Osaka (JP)

( * ) Notice: Subject to any disclaimer, the term of this patent is extended or adjusted under 35 U.S.C. 154(b) by 0 days.

(21) Appl. No.: 15/501,512

(22) PCT Filed: Aug. 4, 2015

(86) PCT No.: PCT/JP2015/072107
§ 371 (c)(1),
(2) Date: Feb. 3, 2017

(87) PCT Pub. No.: WO2016/021604
PCT Pub. Date: Feb. 11, 2016

(65) Prior Publication Data
US 2017/0218411 A1    Aug. 3, 2017

(30) Foreign Application Priority Data
Aug. 4, 2014   (JP) .................... 2014-158398

(51) Int. Cl.
| | | |
|---|---|---|
| *C12P 7/40* | (2006.01) | |
| *C12P 7/62* | (2006.01) | |
| *C12N 15/74* | (2006.01) | |
| *C12N 9/88* | (2006.01) | |

(52) U.S. Cl.
CPC .............. *C12P 7/625* (2013.01); *C12N 15/74* (2013.01); *C12N 9/88* (2013.01)

(58) Field of Classification Search
None
See application file for complete search history.

(56) References Cited

U.S. PATENT DOCUMENTS

| | | |
|---|---|---|
| 5,292,860 A | 3/1994 | Shiotani et al. |
| 5,942,660 A | 8/1999 | Gruys et al. |
| 5,981,257 A | 11/1999 | Fukui et al. |
| 2013/0071892 A1 | 3/2013 | Fukui et al. |

FOREIGN PATENT DOCUMENTS

| | | |
|---|---|---|
| EP | 2295536 A1 | 3/2011 |
| EP | 2540835 A1 | 1/2013 |
| EP | 2963119 A1 | 1/2015 |
| JP | 05-093049 A | 4/1993 |
| JP | 07-265065 A | 10/1995 |
| JP | 3062459 B2 | 4/1998 |
| JP | 2008-029218 A | 2/2008 |
| JP | 2008-086238 A | 4/2008 |
| WO | WO 2011/105379 A1 | 9/2011 |
| WO | WO 2012/099934 A2 | 7/2012 |
| WO | WO 2012/135731 A2 | 10/2012 |

OTHER PUBLICATIONS

Ouyang et al. (Macromol. Symp., 2005, vol. 224, pp. 21-34).*
Budde et al., "Production of Poly(3-Hydroxybutyrate-co-3-Hydroxyhexanoate) from Plant Oil by Engineered *Ralstonia eutropha* Strains," Applied and Environmental Microbiology, May 2011, 77(9):2847-2854.
Kawashima et al., "Characterization and Functional Analyses of R-Specific Enoyl Coenzyme A Hydratases in Polyhydroxyalkanoate-Producing *Ralstonia eutropha*," Applied and Environmental Microbiology, Jan. 15, 2012, 78(2):493-502.
Lopar et al. "Study of metabolic network of *Cupriavidus necator* DSM 545 growing on glycerol by applying elementary flux modes and yield space analysis," J. Ind. Microbiol. Biotechnol., Apr. 9, 2014, 41(6):913-930.
Sato et al. "Construction of a stable plasmid vector for industrial production of poly(3-hydroxybutyrate-co-3-hydroxyhexanoate) by a recombinant *Cupriavidus necator* H16 strain," Journal of Bioscience and Bioengineering, Dec. 1, 2013, 116(6):677-681.
Sato et al., "Regulation of 3-hydroxyhexanoate composition in PHGH synthesized by recombinant *Cupriavidus necator* H16 from plant oil by using butyrate as a co-substrate," Journal of Bioscience and Bioengineering, Sep. 1, 2015, 120(3):246-251.
Spoljaric et al., "In silico optimization and low structured kinetic model of poly[®-3-hydroxybutyrate] synthesis by *Cupriavidus necator* DSM 545 by fed-batch cultivation on glycerol," Journal of Biotechnology, Dec. 1, 2013, 168(4):625-635.
Doi et al., "Microbial Synthesis and Characterization of Poly(3-hydroxybutyrate-co-3-hydroxyhexanoate)," Macromolecules, Jun. 1, 1995, 28:4822-4828.
Fukui et al., "Efficient production of polyhydroxyalkanoates from plant oils by *Alcaligenes eutrophus* and its recombinant strain," Appl. Microbiol. Biotechnol., Apr. 1998, 49:333-336.

(Continued)

*Primary Examiner* — Hope A Robinson
(74) *Attorney, Agent, or Firm* — Foley & Lardner LLP

(57) ABSTRACT

Provided are a method for enhancing the production quantity of poly(3-hydroxybutyrate-co-3-hydroxyhexanoate) (P(3HB-co-3HH)) having a high fraction of 3-hydroxyhexanoate (3HH) using a saccharide or glycerol as a starting material; a method for producing a P(3HB-co-3HH) copolymer including performing transformation by homologous recombination of a crotonyl-CoA reductase gene in a chromosome of a recombinant strain of *Cupriavidus necator* endowed with the ability to produce P(3HB-co-3HH), or performing transformation by introducing an autonomous replication vector in which the crotonyl-CoA reductase gene is incorporated in the aforementioned strain, and cultivating the transformant in a medium containing a saccharide or glycerol as a carbon source; and a method for enhancing the production quantity of the copolymer and/or the fraction of 3HHx in the copolymer.

2 Claims, 2 Drawing Sheets
Specification includes a Sequence Listing.

(56) References Cited

OTHER PUBLICATIONS

Insomphun et al., "Modification of beta-oxidation pathway in *Ralstonia eutropha* for production of poly(3-hydroxybutyrate-co-3-hydroxyhexanoate) from soybean oil," Journal of Bioscience and Bioengineering, 2014 (online Aug. 30, 2013), 117(2):184-190.

Kawashima et al., "Characterization and Functional Analyses of R-Specific Enoyl Coenzyme A Hydratases in Polyhydroxyalkanoate-Producing *Ralstonia eutropha*," Applied and Environmental Microbiology, Jan. 2012 (online Nov. 11, 2011), 78(2):493-502.

Mifune et al., "Engineering of pha operon on *Cupriavidus necator* chromosome for efficient biosynthesis of poly(3-hydroxybutyrate-co-3-hydroxyhexanoate) from vegetable oil," Polymer Degradation and Stability, Mar. 1, 2010, 95:1305-1312.

Qiu et al. "Production of poly(3-hydroxybutyrate-co-3-hydroxyhexanoate) from gluconate and glucose by recombinant *Aeromonas hydrophila* and *Pseudomonas putida*," Biotechnology Letters, Sep. 2005, 27:1381-1386.

Tajima et al., "Isolation and Characterization of *Bacillus* sp. INT005 Accumulating Polyhydroxyalkanoate (PHA) from Gas Field Soil," Journal of Bioscience and Bioengineering, Sep. 10, 2003, 95(1):77-81.

Erb et al., "Carboxylation mechanism and stereochemistry of crotonyl-CoA carboxylase/reductase, a carboxylating enoyl-thioester reductase," PNAS, Jun. 2, 2009, 106(22):8871-8876.

Fukui et al., "Engineering of *Ralstonia eutropha* for Production of Poly(3-hydroxybutyrate-co-3-hydroxyhexanoate) from Fructose and Solid-State Properties of the Copolymer," Biomacromolecules, 2002, 3:618-624.

Fukui, Toshiaki, "Microbial Synthesis of Optically Active Polyesters and 3-Hydroxyalkanoic Acids," Fine Chemicals, 2009, 38(5):32-42.

Insomphun et al., "Improved artificial pathway for biosynthesis of poly(3-hydroxybutyrate-co-3-hydroxyhexanoate) with high $C_6$-monomer composition from fructose in *Ralstonia eutropha*," Metabolic Engineering, 2015, 27:38-45.

Linster et al., "Ethylmalonyl-CoA Decarboxylase, a New Enzyme Involved in Metabolite Proofreading," The Journal of Biological Chemistry, Dec. 16, 2011, 286(10):42992-43003.

\* cited by examiner

SEQUENCE LISTING

<160> NUMBER OF SEQ ID NOS: 40

<210> SEQ ID NO 1
<211> LENGTH: 1362
<212> TYPE: DNA
<213> ORGANISM: Streptomyces cinnamonensis

<400> SEQUENCE: 1

```
gtgaaggaaa tcctggacgc gattcaggcc cagaccgcga ccgcgagcgg caccgccgcg      60
gtcacgtccg ccgacttcgc cgctctcccc ctgcccgact cgtaccgcgc gatcaccgtg     120
cacaaggacg agacggagat gttcgcgggc ctcgagtccc gtgacaagga cccccgcaag     180
tcgctccatc tggacgacgt gccgatcccc gaactcggcc ccggtgaggc cttggtggcc     240
gtcatggcct cctcggtcaa ctacaactcc gtgtggacct cgatcttcga gcccgtctcc     300
accttcagct tcctggagcg gtacggccgg ctcagcgacc tgagcaagcg ccacgacctg     360
ccgtaccaca tcatcggctc cgacctggcg ggcgtcgtgc tgcgcaccgg gcccggcgtg     420
aacgcctgga acccgggcga cgaggtcgtc gcgcactgcc tgagcgtcga gctggagtcc     480
tccgacggcc acaacgacac gatgctcgac cccgagcagc gcatctgggg cttcgagacc     540
aacttcggcg gtctcgccga gatcgcgctc gtcaagtcca accagctcat gccgaagccc     600
ggtcacctga gctgggagga ggccgcctcg cccggcctgg tgaactccac cgcgtaccgc     660
cagctggtgt cccgcaacgg cgccggcatg aagcagggcg acaacgtgct gatctggggc     720
gcgagcggcg gactcgggtc gtacgccacg cagttcgcgc tcgccggcgg cgccaacccc     780
atctgtgtcg tctccagccc ccagaaggcg gagatctgcc gcgcgatggg cgccgaggcg     840
atcatcgacc gcaacgccga gggctacaag ttctggaagg acgagcagac ccaggacccc     900
aaggagtgga agcgcttcgg caagcgcatc cgcgagctca ccgggcggcg aggactcgac     960
atcgtcttcg agcaccccgg ccgcgagacc ttcggcgcct cggtctacgt cacgcgcaag    1020
ggcggcacca tcaccacctg cgcctcgacc tcgggctaca tgcacgagta cgacaaccgc    1080
tacctgtgga tgtccctgaa gcgcatcatc ggctcgcact tcgccaacta ccgcgaggcg    1140
tgggaggcca accgcctgat cgccaagggc aagatccacc cgacgctctc caagacgtac    1200
cgcctggagg acaccggcca ggccgcctac gacgtccacc gcaacctcca ccagggcaag    1260
```

```
gtcggcgtcc tcgccctcgc gcccgaggag ggcctgggcg tgcgcgaccc ggagaagcgg    1320
gcccagcaca tcgacgcgat caaccgtttc cgcaacgtct ga                        1362

<210> SEQ ID NO 2
<211> LENGTH: 1299
<212> TYPE: DNA
<213> ORGANISM: Methylobacterium extorquens

<400> SEQUENCE: 2
atggctgcaa gcgcagcacc ggcctggacc gggcagacgg cggaagccaa ggacctttac      60
gagctcggcg agatccccccc gctcggccac gtgcctgcca agatgtatgc ctgggcgatc    120
cgccgcgagc gccacgggcc gccggagcag tcgcaccagc tcgaagtgct tcccgtctgg    180
gagatcggcg acgacgaggt gctcgtctac gtcatggccg cgggcgtgaa ctacaacggc    240
gtttgggccg gcctgggcga gcctatctcg ccgttcgacg tgcacaaggg cgagtaccac    300
atcgccggct cggacgcgtc gggtatcgtc tggaaggtcg cgccaaggt gaagcgctgg     360 aaggtcggcg acgaggtcat cgtccattgt aaccaggacg acggcgacga cgaggagtgc    420
aacggcggcg atccgatgtt ctcgccgacc cagcggatct ggggttacga ccggcgac     480 ggttcgttcg cgcagttctg ccgggtgcag tcgcgtcagc tcatggcccg ccccaagcac    540
ctgacctggg aagaggccgc ctgctacacg ctgacgctcg ccaccgccta ccgcatgctg    600
ttcggccacg cgccgcacac cgtgcgtccg gccagaacg tgctgatctg gggcgcctcc    660
ggcggcctcg gcgtgttcgg cgtccagctc tgcgcggcct ccggcgccaa cgccatcgcc    720
gtgatctcgg acgagtcgaa gcgcgactac gtgatgagcc tcggtgcgaa gggcgtcatc    780
aaccgcaagg acttcgactg ctgggtcag ctcccgaccg tcaacagccc cgaatacaac    840
acctggctca aggaagcccg gaagttcggc aaggcgatct gggacatcac cggcaagggc    900
aacgacgtcg acatcgtgtt cgagcatccc ggagaggcga ccttcccggt ctcgacgctg    960
gtggccaagc gcgcggcat gatcgtgttc tgcgccggca ccaccggctt caacatcacc    1020
ttcgacgccc ggtacgtctg gatgcggcag aagcgcatcc agggctcgca cttcgcccac    1080
ctcaagcagg cctcggccgc caaccagttc gtgatggacc ggcgcgtcga tccctgcatg    1140
agcgaggtgt tccctggga caagatcccg gcggcccaca ccaagatgtg aagaaccag     1200 cacccgccgg gcaacatggc ggtgctcgtc aactccaccc gcgcgggtct gcgcacggtc    1260
gaggacgtga tcgaggccgg cccgctcaag gcgatgtga                            1299

<210> SEQ ID NO 3
<211> LENGTH: 477
<212> TYPE: DNA
<213> ORGANISM: Cupriavidus necator

<400> SEQUENCE: 3
atgcgtacca tcgcatcgct ggaagaactg gaaggcctgc agggccagga ggtcgcggtc       60
agcgactgga tcgaggtgac ccagcagcag gtcaaccagt tgccgatgc caccggcgac     120 caccagtgga ttcacatcga cgtggagcgc gcgaagaagg agtcgcccta tggcggcccg    180
atcgcgcacg gcttcctgac gctgtcgctg ctgcccaagt tcatgcacaa cgcgctgcac    240
atgccgtcga agatcggcgt taactacggc ctgaaccgcg tgcgcttcac ggcacccgtg    300
ccggtgggca gcaagctgcg cgcgcgcatc aagctgctga aggtcgagcg tctcgatccg    360
ctgccgaagt cgcccgaact ggttggcgca cagtcgacct gggaagtcac ggtggagcgc    420 aaggcagcg accgtccggt ctgtgtcgcc gagtcgatca cgcgccgcta cgggtga        477
```

<210> SEQ ID NO 4
<211> LENGTH: 900
<212> TYPE: DNA
<213> ORGANISM: Mouse

<400> SEQUENCE: 4

| | | |
|---|---|---|
| atggccaagt gcctgctgac gtccagcctg agcgtgcgga ccaagctgct ccagaccggc | 60 |
| gtgtcgctgt acaacacgtc gcatgggttc cacgaggagg aggtcaagaa gatcctggag | 120 |
| cagtttccgg gcggctcgat cgacctgctg aagaagcaga acggcatcgg catcctcacg | 180 |
| ctgaacaacc cgaacaagat gaacgcgttc tccggggtga tgatgctcca gctgctggag | 240 |
| cgcgtgatcg aactggagaa ctggaccgaa ggcaaaggcc tcatcatcca tggcgcgaag | 300 |
| aacaccttct gctcggggtc ggacctgaat gccgtgaaag ccctgagcac gccggaatcg | 360 |
| ggcgtggcgc tgagcatgtt catgcagaac accctgaccc gcttcatgcg gctgccgctg | 420 |
| atctcggtcg cactggtgca aggctgggcc atgggcggcg cgccgaact gacgaccgcg | 480 |
| tgcgactttc gcctgatgac ggaggagtcg gtcattcgct tcgtgcacaa ggagatgggc | 540 |
| atcgtcccgt cgtggggcgg cacctcccgc ctggtggaga tcatcggcag ccgccaagcg | 600 |
| ctgaaggtcc tgagcggcac cctgaagctg gactcgaagg aggccctgaa catcggcctg | 660 |
| accgatgagg tgctccagcc gtcggacgaa accaccgccc tggaacaggc ccaggaatgg | 720 |
| ctggagaagt tcgtgagcgg cccgccccag gtcattcgcg gcctgaagaa gtccgtgtgc | 780 |
| agcgcacgcg agctgtatat cgaggaggcg ctccagaatg aacgcgatgt gctggaaacg | 840 |
| ctgtggggcg gccccgccaa tctggaagcc atcgcgaaga agggcaagca caccaagtag | 900 |

<210> SEQ ID NO 5
<211> LENGTH: 47
<212> TYPE: DNA
<213> ORGANISM: Artificial Sequence
<220> FEATURE:
<223> OTHER INFORMATION: Oligonucleotide primer used in PCR

<400> SEQUENCE: 5
tacatggatc caagggaggc aaagtcatga cgcgtgaagt ggtagtg        47

<210> SEQ ID NO 6
<211> LENGTH: 36
<212> TYPE: DNA
<213> ORGANISM: Artificial Sequence
<220> FEATURE:
<223> OTHER INFORMATION: Oligonucleotide primer used in PCR

<400> SEQUENCE: 6
ggatcatatg cttcctcaga tacgctcgaa gatggc        36

<210> SEQ ID NO 7
<211> LENGTH: 35
<212> TYPE: DNA
<213> ORGANISM: Artificial Sequence
<220> FEATURE:
<223> OTHER INFORMATION: Oligonucleotide primer used in PCR

<400> SEQUENCE: 7
tttggaattc tacctaggga tcaaattaga ggaaa        35

<210> SEQ ID NO 8
<211> LENGTH: 41
<212> TYPE: DNA

<213> ORGANISM: Artificial Sequence
<220> FEATURE:
<223> OTHER INFORMATION: Oligonucleotide primer used in PCR

<400> SEQUENCE: 8
ccttactgca tgtgcctgct tcattctcgt aaagttgaaa g          41

<210> SEQ ID NO 9
<211> LENGTH: 34
<212> TYPE: DNA
<213> ORGANISM: Artificial Sequence
<220> FEATURE:
<223> OTHER INFORMATION: Oligonucleotide primer used in PCR

<400> SEQUENCE: 9
gaatgaagca ggcacatgca gtaagggtgc tggg                  34

<210> SEQ ID NO 10
<211> LENGTH: 45
<212> TYPE: DNA
<213> ORGANISM: Artificial Sequence
<220> FEATURE:
<223> OTHER INFORMATION: Oligonucleotide primer used in PC

<400> SEQUENCE: 10
tcctaagctt gctgaccgtg atcgtcgaca actttgaaga cctga      45

<210> SEQ ID NO 11
<211> LENGTH: 40
<212> TYPE: DNA
<213> ORGANISM: Artificial Sequence
<220> FEATURE:
<223> OTHER INFORMATION: Oligonucleotide primer used in PCR

<400> SEQUENCE: 11
acgaattcag gaggaacctg gatgaaggaa atcctggacg            40

<210> SEQ ID NO 12
<211> LENGTH: 29
<212> TYPE: DNA
<213> ORGANISM: Artificial Sequence
<220> FEATURE:
<223> OTHER INFORMATION: Oligonucleotide primer used in PCR

<400> SEQUENCE: 12
aggtctagag tgcgttcaga cgttgcgga                        29

<210> SEQ ID NO 13
<211> LENGTH: 41
<212> TYPE: DNA
<213> ORGANISM: Artificial Sequence
<220> FEATURE:
<223> OTHER INFORMATION: Oligonucleotide primer used in PCR

<400> SEQUENCE: 13
acgaattcag gaggaacctg gatggctgca agcgcagcac c          41

<210> SEQ ID NO 14
<211> LENGTH: 27
<212> TYPE: DNA
<213> ORGANISM: Artificial Sequence
<220> FEATURE:
<223> OTHER INFORMATION: Oligonucleotide primer used in PCR

<400> SEQUENCE: 14
aggtctagat cacatcgcct tgagcgg                          27

<210> SEQ ID NO 15
<211> LENGTH: 31
<212> TYPE: DNA
<213> ORGANISM: Artificial Sequence
<220> FEATURE:
<223> OTHER INFORMATION: Oligonucleotide primer used in PCR

<400> SEQUENCE: 15
atacatatgg ctgcaagcgc agcaccggcc t                          31

<210> SEQ ID NO 16
<211> LENGTH: 30
<212> TYPE: DNA
<213> ORGANISM: Artificial Sequence
<220> FEATURE:
<223> OTHER INFORMATION: Oligonucleotide primer used in PCR

<400> SEQUENCE: 16
tatgaattct cacatcgcct tgagcgggcc                            30

<210> SEQ ID NO 17
<211> LENGTH: 31
<212> TYPE: DNA
<213> ORGANISM: Artificial Sequence
<220> FEATURE:
<223> OTHER INFORMATION: Oligonucleotide primer used in PCR

<400> SEQUENCE: 17
cccaagcttt atcgtcaaga ggagactatc g                          31

<210> SEQ ID NO 18
<211> LENGTH: 36
<212> TYPE: DNA
<213> ORGANISM: Artificial Sequence
<220> FEATURE:
<223> OTHER INFORMATION: Oligonucleotide primer used in PCR

<400> SEQUENCE: 18
cccaagcttg gatcctcacc cgtagcggcg cgtgat                     36

<210> SEQ ID NO 19
<211> LENGTH: 37
<212> TYPE: DNA
<213> ORGANISM: Artificial Sequence
<220> FEATURE:
<223> OTHER INFORMATION: Oligonucleotide primer used in PCR

<400> SEQUENCE: 19
ggaattctat tgaggtggcc gcgaatatcg gcagcct                    37

<210> SEQ ID NO 20
<211> LENGTH: 33
<212> TYPE: DNA
<213> ORGANISM: Artificial Sequence
<220> FEATURE:
<223> OTHER INFORMATION: Oligonucleotide primer used in PCR

<400> SEQUENCE: 20
ggaattcagg tgcgcttcga caagtcatac ttt                        33

<210> SEQ ID NO 21
<211> LENGTH: 36
<212> TYPE: DNA
<213> ORGANISM: Artificial Sequence
<220> FEATURE:

-continued

<223> OTHER INFORMATION: Oligonucleotide primer used in PCR

<400> SEQUENCE: 21
ggccaaccag cgcgcgcccc gccggcggcg tctcgt                36

<210> SEQ ID NO 22
<211> LENGTH: 27
<212> TYPE: DNA
<213> ORGANISM: Artificial Sequence
<220> FEATURE:
<223> OTHER INFORMATION: Oligonucleotide primer used in PCR

<400> SEQUENCE: 22
gcatgctgtt ctcgatggca ctgacct                27

<210> SEQ ID NO 23
<211> LENGTH: 25
<212> TYPE: DNA
<213> ORGANISM: Artificial Sequence
<220> FEATURE:
<223> OTHER INFORMATION: Oligonucleotide primer used in PCR

<400> SEQUENCE: 23
tgcagttcgt atgcgaccgc atcga                25

<210> SEQ ID NO 24
<211> LENGTH: 33
<212> TYPE: DNA
<213> ORGANISM: Artificial Sequence
<220> FEATURE:
<223> OTHER INFORMATION: Oligonucleotide primer used in PCR

<400> SEQUENCE: 24
ggaattcagg tgcgcttcga caagtcatac ttt                33

<210> SEQ ID NO 25
<211> LENGTH: 31
<212> TYPE: DNA
<213> ORGANISM: Artificial Sequence
<220> FEATURE:
<223> OTHER INFORMATION: Oligonucleotide primer used in PCR

<400> SEQUENCE: 25
tgcccggcac gcccggcaac cggcggctcg a                31

<210> SEQ ID NO 26
<211> LENGTH: 30
<212> TYPE: DNA
<213> ORGANISM: Artificial Sequence
<220> FEATURE:
<223> OTHER INFORMATION: Oligonucleotide primer used in PCR

<400> SEQUENCE: 26
tgcgaatcct cgtaggtacc agagtgtgga                30

<210> SEQ ID NO 27
<211> LENGTH: 32
<212> TYPE: DNA
<213> ORGANISM: Artificial Sequence
<220> FEATURE:
<223> OTHER INFORMATION: Oligonucleotide primer used in PCR

<400> SEQUENCE: 27
ataccgtcga cggtgctggc tccggaaggt tt                32

<210> SEQ ID NO 28
<211> LENGTH: 32
<212> TYPE: DNA
<213> ORGANISM: Artificial Sequence
<220> FEATURE:
<223> OTHER INFORMATION: Oligonucleotide primer used in PCR

<400> SEQUENCE: 28
ctgcagtcga ccctgcgcgc ccacgccgct tt                                    32

<210> SEQ ID NO 29
<211> LENGTH: 24
<212> TYPE: DNA
<213> ORGANISM: Artificial Sequence
<220> FEATURE:
<223> OTHER INFORMATION: Oligonucleotide primer used in PCR

<400> SEQUENCE: 29
gcgggcaacg gatggaggta agca                                             24

<210> SEQ ID NO 30
<211> LENGTH: 26
<212> TYPE: DNA
<213> ORGANISM: Artificial Sequence
<220> FEATURE:
<223> OTHER INFORMATION: Oligonucleotide primer used in PCR

<400> SEQUENCE: 30
cttacctcca tccgttgccc gcttcg                                           26

<210> SEQ ID NO 31
<211> LENGTH: 20
<212> TYPE: DNA
<213> ORGANISM: Artificial Sequence
<220> FEATURE:
<223> OTHER INFORMATION: Oligonucleotide primer used in PCR

<400> SEQUENCE: 31
atgagtcaaa catcaacctt                                                  20

<210> SEQ ID NO 32
<211> LENGTH: 22
<212> TYPE: DNA
<213> ORGANISM: Artificial Sequence
<220> FEATURE:
<223> OTHER INFORMATION: Oligonucleotide primer used in PCR

<400> SEQUENCE: 32
ttattcgtcg tgttcttccc ac                                               22

<210> SEQ ID NO 33
<211> LENGTH: 20
<212> TYPE: DNA
<213> ORGANISM: Artificial Sequence
<220> FEATURE:
<223> OTHER INFORMATION: Oligonucleotide primer used in PCR

<400> SEQUENCE: 33
tcgaccggcg ccgacttctc                                                  20

<210> SEQ ID NO 34
<211> LENGTH: 21
<212> TYPE: DNA
<213> ORGANISM: Artificial Sequence
<220> FEATURE:
<223> OTHER INFORMATION: Oligonucleotide primer used in PCR -continued

<400> SEQUENCE: 34
gcatgccagt gtcttacttc t                                              21

<210> SEQ ID NO 35
<211> LENGTH: 20
<212> TYPE: DNA
<213> ORGANISM: Artificial Sequence
<220> FEATURE:
<223> OTHER INFORMATION: Oligonucleotide primer used in PCR

<400> SEQUENCE: 35
cgccgcatga cgcttgcata                                                20

<210> SEQ ID NO 36
<211> LENGTH: 24
<212> TYPE: DNA
<213> ORGANISM: Artificial Sequence
<220> FEATURE:
<223> OTHER INFORMATION: Oligonucleotide primer used in PCR

<400> SEQUENCE: 36
ccatatgcgg ccccggaaaa cccc                                           24

<210> SEQ ID NO 37
<211> LENGTH: 453
<212> TYPE: PRT
<213> ORGANISM: Streptomyces cinnamonensis

<400> SEQUENCE: 37

Met Lys Glu Ile Leu Asp Ala Ile Gln Ala Gln Thr Ala Thr Ala Ser
1               5                   10                  15

Gly Thr Ala Ala Val Thr Ser Ala Asp Phe Ala Ala Leu Pro Leu Pro
            20                  25                  30

Asp Ser Tyr Arg Ala Ile Thr Val His Lys Asp Glu Thr Glu Met Phe
        35                  40                  45

Ala Gly Leu Glu Ser Arg Asp Lys Asp Pro Arg Lys Ser Leu His Leu
    50                  55                  60

Asp Asp Val Pro Ile Pro Glu Leu Gly Pro Gly Glu Ala Leu Val Ala
65                  70                  75                  80

Val Met Ala Ser Ser Val Asn Tyr Asn Ser Val Trp Thr Ser Ile Phe
                85                  90                  95

Glu Pro Val Ser Thr Phe Ser Phe Leu Glu Arg Tyr Gly Arg Leu Ser
            100                 105                 110

Asp Leu Ser Lys Arg His Asp Leu Pro Tyr His Ile Ile Gly Ser Asp
        115                 120                 125

Leu Ala Gly Val Val Leu Arg Thr Gly Pro Gly Val Asn Ala Trp Asn
    130                 135                 140

Pro Gly Asp Glu Val Val Ala His Cys Leu Ser Val Glu Leu Glu Ser
145                 150                 155                 160

Ser Asp Gly His Asn Asp Thr Met Leu Asp Pro Glu Gln Arg Ile Trp
                165                 170                 175

Gly Phe Glu Thr Asn Phe Gly Gly Leu Ala Glu Ile Ala Leu Val Lys
            180                 185                 190

Ser Asn Gln Leu Met Pro Lys Pro Gly His Leu Ser Trp Glu Glu Ala
        195                 200                 205

Ala Ser Pro Gly Leu Val Asn Ser Thr Ala Tyr Arg Gln Leu Val Ser
    210                 215                 220

Arg Asn Gly Ala Gly Met Lys Gln Gly Asp Asn Val Leu Ile Trp Gly

```
             225                 230                 235                 240
        Ala Ser Gly Gly Leu Gly Ser Tyr Ala Thr Gln Phe Ala Leu Ala Gly
                        245                 250                 255

Gly Ala Asn Pro Ile Cys Val Val Ser Ser Pro Gln Lys Ala Glu Ile
                        260                 265                 270

Cys Arg Ala Met Gly Ala Glu Ala Ile Ile Asp Arg Asn Ala Glu Gly
                        275                 280                 285

Tyr Lys Phe Trp Lys Asp Glu Gln Thr Gln Asp Pro Lys Glu Trp Lys
                        290                 295                 300

Arg Phe Gly Lys Arg Ile Arg Glu Leu Thr Gly Arg Arg Gly Leu Asp
        305                 310                 315                 320

Ile Val Phe Glu His Pro Gly Arg Glu Thr Phe Gly Ala Ser Val Tyr
                        325                 330                 335

Val Thr Arg Lys Gly Gly Thr Ile Thr Thr Cys Ala Ser Thr Ser Gly
                        340                 345                 350

Tyr Met His Glu Tyr Asp Asn Arg Tyr Leu Trp Met Ser Leu Lys Arg
                        355                 360                 365

Ile Ile Gly Ser His Phe Ala Asn Tyr Arg Glu Ala Trp Glu Ala Asn
                        370                 375                 380

Arg Leu Ile Ala Lys Gly Lys Ile His Pro Thr Leu Ser Lys Thr Tyr
        385                 390                 395                 400

Arg Leu Glu Asp Thr Gly Gln Ala Ala Tyr Asp Val His Arg Asn Leu
                        405                 410                 415

His Gln Gly Lys Val Gly Val Leu Ala Leu Ala Pro Glu Gly Leu
                        420                 425                 430

Gly Val Arg Asp Pro Glu Lys Arg Ala Gln His Ile Asp Ala Ile Asn
                        435                 440                 445

Arg Phe Arg Asn Val
                        450

<210> SEQ ID NO 38
<211> LENGTH: 432
<212> TYPE: PRT
<213> ORGANISM: Methylobacterium extorquens

<400> SEQUENCE: 38

Met Ala Ala Ser Ala Ala Pro Ala Trp Thr Gly Gln Thr Ala Glu Ala
        1               5                   10                  15

Lys Asp Leu Tyr Glu Leu Gly Glu Ile Pro Pro Leu Gly His Val Pro
                        20                  25                  30

Ala Lys Met Tyr Ala Trp Ala Ile Arg Arg Glu Arg His Gly Pro Pro
                        35                  40                  45

Glu Gln Ser His Gln Leu Glu Val Leu Pro Val Trp Glu Ile Gly Asp
                        50                  55                  60

Asp Glu Val Leu Val Tyr Val Met Ala Ala Gly Val Asn Tyr Asn Gly
        65                  70                  75                  80

Val Trp Ala Gly Leu Gly Glu Pro Ile Ser Pro Phe Asp Val His Lys
                        85                  90                  95

Gly Glu Tyr His Ile Ala Gly Ser Asp Ala Ser Gly Ile Val Trp Lys
                        100                 105                 110

Val Gly Ala Lys Val Lys Arg Trp Lys Val Gly Asp Glu Val Ile Val
                        115                 120                 125

His Cys Asn Gln Asp Asp Gly Asp Asp Glu Glu Cys Asn Gly Gly Asp
                        130                 135                 140
```

Pro Met Phe Ser Pro Thr Gln Arg Ile Trp Gly Tyr Glu Thr Gly Asp
145                 150                 155                 160

Gly Ser Phe Ala Gln Phe Cys Arg Val Gln Ser Arg Gln Leu Met Ala
            165                 170                 175

Arg Pro Lys His Leu Thr Trp Glu Glu Ala Ala Cys Tyr Thr Leu Thr
        180                 185                 190

Leu Ala Thr Ala Tyr Arg Met Leu Phe Gly His Ala Pro His Thr Val
        195                 200                 205

Arg Pro Gly Gln Asn Val Leu Ile Trp Gly Ala Ser Gly Gly Leu Gly
    210                 215                 220

Val Phe Gly Val Gln Leu Cys Ala Ala Ser Gly Ala Asn Ala Ile Ala
225                 230                 235                 240

Val Ile Ser Asp Glu Ser Lys Arg Asp Tyr Val Met Ser Leu Gly Ala
            245                 250                 255

Lys Gly Val Ile Asn Arg Lys Asp Phe Asp Cys Trp Gly Gln Leu Pro
        260                 265                 270

Thr Val Asn Ser Pro Glu Tyr Asn Thr Trp Leu Lys Glu Ala Arg Lys
    275                 280                 285

Phe Gly Lys Ala Ile Trp Asp Ile Thr Gly Lys Gly Asn Asp Val Asp
290                 295                 300

Ile Val Phe Glu His Pro Gly Glu Ala Thr Phe Pro Val Ser Thr Leu
305                 310                 315                 320

Val Ala Lys Arg Gly Met Ile Val Phe Cys Ala Gly Thr Thr Gly
            325                 330                 335

Phe Asn Ile Thr Phe Asp Ala Arg Tyr Val Trp Met Arg Gln Lys Arg
        340                 345                 350

Ile Gln Gly Ser His Phe Ala His Leu Lys Gln Ala Ser Ala Ala Asn
    355                 360                 365

Gln Phe Val Met Asp Arg Arg Val Asp Pro Cys Met Ser Glu Val Phe
370                 375                 380

Pro Trp Asp Lys Ile Pro Ala Ala His Thr Lys Met Trp Lys Asn Gln
385                 390                 395                 400

His Pro Pro Gly Asn Met Ala Val Leu Val Asn Ser Thr Arg Ala Gly
            405                 410                 415

Leu Arg Thr Val Glu Asp Val Ile Glu Ala Gly Pro Leu Lys Ala Met
        420                 425                 430

<210> SEQ ID NO 39
<211> LENGTH: 158
<212> TYPE: PRT
<213> ORGANISM: Cupriavidus necator

<400> SEQUENCE: 39

Met Arg Thr Ile Ala Ser Leu Glu Glu Leu Glu Gly Leu Gln Gly Gln
1               5                   10                  15

Glu Val Ala Val Ser Asp Trp Ile Glu Val Thr Gln Gln Val Asn
            20                  25                  30

Gln Phe Ala Asp Ala Thr Gly Asp His Gln Trp Ile His Ile Asp Val
        35                  40                  45

Glu Arg Ala Lys Lys Glu Ser Pro Tyr Gly Gly Pro Ile Ala His Gly
    50                  55                  60

Phe Leu Thr Leu Ser Leu Leu Pro Lys Phe Met His Asn Ala Leu His
65                  70                  75                  80

Met Pro Ser Lys Ile Gly Val Asn Tyr Gly Leu Asn Arg Val Arg Phe
            85                  90                  95

Thr Ala Pro Val Pro Val Gly Ser Lys Leu Arg Ala Arg Ile Lys Leu
                100                 105                 110

Leu Lys Val Glu Arg Leu Asp Pro Leu Pro Lys Ser Pro Glu Leu Val
            115                 120                 125

Gly Ala Gln Ser Thr Trp Glu Val Thr Val Glu Arg Glu Gly Ser Asp
130                 135                 140

Arg Pro Val Cys Val Ala Glu Ser Ile Thr Arg Arg Tyr Gly
145                 150                 155

<210> SEQ ID NO 40
<211> LENGTH: 299
<212> TYPE: PRT
<213> ORGANISM: Mouse

<400> SEQUENCE: 40

Met Ala Lys Cys Leu Leu Thr Ser Ser Leu Ser Val Arg Thr Lys Leu
1               5                   10                  15

Leu Gln Thr Gly Val Ser Leu Tyr Asn Thr Ser His Gly Phe His Glu
            20                  25                  30

Glu Glu Val Lys Lys Ile Leu Glu Gln Phe Pro Gly Gly Ser Ile Asp
        35                  40                  45

Leu Leu Lys Lys Gln Asn Gly Ile Gly Ile Leu Thr Leu Asn Asn Pro
50                  55                  60

Asn Lys Met Asn Ala Phe Ser Gly Val Met Met Leu Gln Leu Leu Glu
65                  70                  75                  80

Arg Val Ile Glu Leu Glu Asn Trp Thr Glu Gly Lys Gly Leu Ile Ile
                85                  90                  95

His Gly Ala Lys Asn Thr Phe Cys Ser Gly Ser Asp Leu Asn Ala Val
            100                 105                 110

Lys Ala Leu Ser Thr Pro Glu Ser Gly Val Ala Leu Ser Met Phe Met
        115                 120                 125

Gln Asn Thr Leu Thr Arg Phe Met Arg Leu Pro Leu Ile Ser Val Ala
130                 135                 140

Leu Val Gln Gly Trp Ala Met Gly Gly Gly Ala Glu Leu Thr Thr Ala
145                 150                 155                 160

Cys Asp Phe Arg Leu Met Thr Glu Glu Ser Val Ile Arg Phe Val His
                165                 170                 175

Lys Glu Met Gly Ile Val Pro Ser Trp Gly Gly Thr Ser Arg Leu Val
            180                 185                 190

Glu Ile Ile Gly Ser Arg Gln Ala Leu Lys Val Leu Ser Gly Thr Leu
        195                 200                 205

Lys Leu Asp Ser Lys Glu Ala Leu Asn Ile Gly Leu Thr Asp Glu Val
210                 215                 220

Leu Gln Pro Ser Asp Glu Thr Thr Ala Leu Glu Gln Ala Gln Glu Trp
225                 230                 235                 240

Leu Glu Lys Phe Val Ser Gly Pro Pro Gln Val Ile Arg Gly Leu Lys
                245                 250                 255

Lys Ser Val Cys Ser Ala Arg Glu Leu Tyr Ile Glu Glu Ala Leu Gln
            260                 265                 270

Asn Glu Arg Asp Val Leu Glu Thr Leu Trp Gly Gly Pro Ala Asn Leu
        275                 280                 285

Glu Ala Ile Ala Lys Lys Gly Lys His Thr Lys
290                 295

METHOD FOR PRODUCING POLYHYDROXYALKANOATE COPOLYMER FROM SACCHARIDE RAW MATERIAL

CROSS-REFERENCE TO RELATED APPLICATIONS

This application is a National Stage application of PCT/JP2015/072107, filed Aug. 4, 2015, which claims priority from Japanese application JP 2014-158398, filed Aug. 4, 2014.

The instant application contains a Sequence Listing which has been submitted in ASCII format via EFS-WEB and is hereby incorporated by reference in its entirety. Said ASCII copy, created on Dec. 5, 2018, is named sequence.txt and is 24 KB.

TECHNICAL FIELD

The present invention relates to a method for enhancing the fraction of 3-hydroxyhexanoate in a copolymer by enhancing the production quantity of the copolymer using a saccharide and/or glycerol as a basic raw material in the production by microorganisms of a type of polyhydroxyalkanoate copolymer in the form of poly(3-hydroxybutyrate-co-3-hydroxyhexanoate), which can be degraded by microorganisms and demonstrates superior biocompatibility.

BACKGROUND ART

Plastics are inexpensive materials capable of realizing a diverse range of properties corresponding to the structure thereof, thereby making them indispensable for modern society. However, nearly all plastics are synthesized from petroleum raw materials, and have been developed and produced with the objective of achieving long-term stability. As a result, since the majority of petroleum-based synthetic plastics are not degraded in the natural environment following their disposal, the management and disposal of used plastic waste is becoming a major problem in countries throughout the world. In addition, the depletion of fossil fuels, as represented by petroleum, is also becoming a serious problem. Even if the duration during which fossil fuel resources can be recovered is able to be extended through advances made in the field of mining technology, these resources are still finite, and the consumption of fossil fuel resources is predicted to continue to increase in the future due to increased demand stemming from global economic growth. What is more, rising carbon dioxide levels in the air attributable to consumption of fossil fuel resources is also becoming a significant environmental problem. Consequently, it is necessary to curtail consumption of fossil fuel resources and establish a social structure that is not dependent on fossil fuel resources.

In view of these circumstances, there is a desire to develop and practically implement the use of plastics that reduce the burden on the environment in the form of bioplastics. Bioplastics is the generic term for two types of plastics consisting of "biodegradable plastics" and "biomass plastics". Biodegradable plastics are plastics that are degraded by microorganisms in the environment and do not cause problems in terms of waste disposal as is the case with petroleum-based synthetic plastics. In addition, biomass plastics refer to plastics that use renewable biomass resources derived from plants and animals used as raw materials, and since the carbon dioxide generated by their combustion is carbon dioxide that would have been inherently present in air following the fixation thereof by plant photosynthesis (making it carbon neutral), it can be said to be material capable of contributing to the future establishment of a recycling society from the viewpoints of depletion of fossil fuel resources and discharge of greenhouse gases.

Polyhydroxyalkanoates (PHA), which are accumulated in the cells of numerous microorganisms for use as an energy source, are expected to serve as plastic materials synthesized from biomass as a raw material and is biodegradable. Although poly(3-hydroxybuturate) (P(3HB)) is a typical example of a PHA biosynthesized by various microorganisms, since P(3HB) has the properties of being hard and brittle, its practical application as a material is difficult. On the other hand, since many PHA copolymers, which are hydroxyalkanoates having different structures as comonomer units, have improved flexibility and other properties, many researches have been actively conducted on the biosynthesis of PHA copolymers. For example, poly(3-hydroxybutyrate-co-3-hydroxyvalerate) copolymer is biosynthesized by providing a precursor in the form of propionic acid or pentanoic acid, while poly(3-hydroxybutyrate-co-4-hydroxybutyrate) copolymer is biosynthesized by adding 1,4-butandiol or γ-butyrolactone. More recently, research is proceeding in several countries on the biosynthesis of PHA copolymers by genetically modified microorganisms from biomass in the absence of the addition of precursor.

Poly((R)-3-hydroxybutyrate-co-3-hydroxyhexanoate) copolymer (P(3HB-co-3HHx)), which is biosynthesized by some bacteria such as a soil bacterium *Aeromonas caviae* using vegetable oil or fatty acids as carbon sources, demonstrates an increase in flexibility corresponding to the polymer composition thereof, and a polymer containing a (R)-3-hydroxyhexanoate (3HHx) unit at about 10 mol % has been determined to be a plastic that demonstrates suitably superior flexibility. The fraction of 3HHx of P(3HB-co-3HHx) biosynthesized by *A. caviae* from vegetable oil is present at 10 mol % to 20 mol %, and although this plastic demonstrates flexibility suitable for practical applications, the accumulation thereof in bacterial cells is low at only about 15% by weight, thereby making its application to actual production difficult (see Patent Document 1, Patent Document 2 and Non-Patent Document 1).

Therefore, a recombinant strain that efficiently produces P(3HB-co-3HHx) having a high fraction of 3HHx using vegetable oil as a carbon source was developed by allowing a PHA polymerase having broad substrate specificity to function in *Cupriavidus necator*, which is known to efficiently produce P(3HB), and then modifying the polyester biosynthesis pathway and β-oxidation pathway that decomposes fatty acids (see Patent Document 3, Patent Document 4, Patent Document 5, Patent Document 6, Non-Patent Document 2, Non-Patent Document 3, Non-Patent Document 4 and Non-Patent Document 5).

In the aforementioned research on the microbial synthesis of P(3HB-co-3HHx), long-chain fatty acids, butyric acid or butanol was used as raw materials. On the other hand, technology for the production of P(3HB-co-3HHx) using a saccharide derived from a polysaccharides as raw materials would be extremely important when considering that polysaccharides constitute a reproducible biomass resource that is present in large amounts on the earth. However, although the only reported wild-type strain of microorganism capable of biosynthesizing P(3HB-co-3HHx) from a saccharide raw material is *Bacillus* sp. strain INT005, which produces P(3HB-co-3HHx) from glucose, the fraction of 3HHx is low at 1.6 mol % and its biosynthesis pathway has yet to be unclear (see Non-Patent Document 6).

There are also extremely few reports on the biosynthesis of P(3HB-co-3HHx) from saccharide raw materials by recombinant microorganisms. Qiu et al. reported biosynthesis of P(3HB-co-19 mol % 3HHx) at 10% by weight by a recombinant strain of *Pseudomonas putida* possessing an enzyme which produces (R)-3-hydroxyhexanoyl-CoA ((R)-3HHx-CoA) from an intermediate in fatty acid biosynthesis pathway by transthioesterification, along with (R)-3-hydroxybutyryl-CoA ((R)-3HB-CoA)-generation pathway. They also reported biosynthesis of P(3HB-co-14 mol % 3HHx) at 10% by weight by a recombinant strain of *Aeromonas hydrophila* expressing thioesterase capable of releasing an long acyl group by cleaving acyl-acyl carrier protein intermediates in fatty acid biosynthesis pathway followed by generation of (R)-3HHx-CoA via decomposition of long acyl group thereof (see Non-Patent Document 7).

On the other hand, the inventors of the present invention previously examined biosynthesis of P(3HB-co-3HHx) from fructose raw material by a recombinant strain of *C. necator*. Namely, a pathway was designed to form butyryl-CoA from an intermediate having four carbon atoms formed by condensing two molecules of acetyl-CoA derived from a saccharide, and to generate an intermediate having six carbon atoms by condensing the butyryl-CoA with another molecule of acetyl-CoA, and then to copolymerize (R)-3HHx-CoA produced by further conversion of the six carbon intermediate and (R)-3HB-CoA. In order to establish this artificial metabolic pathway, (R)-specific enoyl-CoA hydratase gene phaJ$_{Ac}$, derived from *A. caviae* producing crotonyl-CoA from (R)-3HB-CoA, and crotonyl-CoA reductase gene ccr$_{Sc}$ derived from an actinomycete *Streptomyces cinnamonensis*, which reduces the double bond of crotonyl-CoA, were introduced into a PHA polymerase-deficient strain PHB$^-$4 along with PHA polymerase gene phaC$_{Ac}$ having broad substrate specificity. As a result, the resulting recombinant strain biosynthesized P(3HB-co-3HHx) containing 1.2 mol % to 1.6 mol % of the 3HHx unit from fructose as the only carbon source, and although the designed pathway was certainly found to be functional, the fraction of 3HHx was too low to improve the polymer properties (Non-Patent Document 8).

PRIOR ART DOCUMENTS

Patent Documents

Patent Document 1: Japanese Unexamined Patent Publication No. H5-93049
Patent Document 2: Japanese Unexamined Patent Publication No. H7-265065
Patent Document 3: Japanese Patent No. 3062459
Patent Document 4: Japanese Unexamined Patent Publication No. 2008-86238
Patent Document 5: Japanese Unexamined Patent Publication No. 2008-29218
Patent Document 6: International Publication No. WO 2011/105379

Non-Patent Documents

Non-Patent Document 1: Doi, Y., et al., Macromolecules, 28: 4822-4828 (1995)
Non-Patent Document 2: Fukui, T. & Doi, Y., Appl. Microbiol. Biotechnol., 49: 333-336 (1998)
Non-Patent Document 3: Mifune, J., et al., Polym. Degrad. Stab., 95: 1305-1312 (2010)
Non-Patent Document 4: Kawashima, Y., et al., Appl. Environ. Microbiol., 78: 493-502 (2012)
Non-Patent Document 5: Insomphun, C., et al., J. Biosci. Bioeng., 117: 184-190 (2014)
Non-Patent Document 6: Tajima, et al., J. Biosci. Bioeng., 95: 77-81 (2005)
Non-Patent Document 7: Qiu, Y. Z., et al., Biotechnol. Lett., 27: 1381-1386 (2005)
Non-Patent Document 8: Fukui, T., et al., Biomacromolecules, 3: 618-624 (2002)

DISCLOSURE OF THE INVENTION

Problems to be Solved by the Invention

As was previously described, although there are many methods for producing P(3HB-co-3HHx) containing a high fraction of 3HHx using vegetable oil or fatty acids as raw materials, there are hardly any such methods that use saccharides or glycerol as raw materials. According to the report by Qiu, et al., although the fraction of 3HHx is sufficiently high, the cellular polymer content is only 20% by weight or less, thereby resulting in low production efficiency. On the other hand, although prior art disclosed by the inventors of the present invention demonstrated large accumulation of the polymer per microbial cell weight of 39% by weight to 49% by weight, the fraction of 3HHx was low at 1.6 mol %, which was inadequate to achieve sufficient flexibility. Thus, it has long been sought to establish a method for producing P(3HB-co-3HHx) with high fractions of 3HHx from a saccharide or glycerol at a high cellular content.

Means for Solving the Problems

Therefore, as a result of completely rethinking the previously proposed novel metabolic pathway, the inventors of the present invention found that a recombinant *C. necator* constructed by introducing crotonyl-CoA reductase gene, (R)-specific enoyl-CoA hydratase gene and ethylmalonyl-CoA decarboxylase gene, and a recombinant *C. necator* strain, in which acetoacetyl-CoA reductase gene (phaB1) in the phaCAB1 operon has been deficient, constructed by introducing a crotonyl-CoA reductase gene, (R)-specific enoyl-CoA hydratase gene and ethylmalonyl-CoA decarboxylase gene, are capable of producing P(3HB-co-3XXh) having a high fraction of 3HHx at a high cellular content on a saccharide or glycerol as a raw material.

Namely, the present invention is as indicated below.

[1] A method for producing poly(3-hydroxybutyrate-co-3-hydroxyhexanote), comprising: transforming a recombinant *Cupriavidus necator* strain imparted with the ability to produce poly(3-hydroxybutyrate-co-3-hydroxyhexanoate) by homologous recombination of crotonyl-CoA reductase gene, (R)-specific enoyl-CoA hydratase gene and ethylmalonyl-CoA decarboxylase gene in a chromosome thereof, or transforming by introducing an autonomously replicating vector having these genes incorporated in that strain, and cultivating the transformant in a medium containing a saccharide and/or glycerol as a carbon source.

[2] A method for producing poly(3-hydroxybutyrate-co-3-hydroxyhexanote), comprising: transforming a recombinant strain deficient in a gene encoding acetoacetyl-CoA reductase in a chromosome of *Cupriavidus necator* strain imparted with the ability to produce poly(3-hydroxybutyrate-co-3-hydroxyhexanoate in a chromosome thereof, or transforming by introducing an autonomously replicating vector having this gene incorporated in that strain, and cultivating the transformant in a medium containing a saccharide and/or glycerol as a carbon source.

[3] The method described in [2] above, further comprising transforming an (R)-specific enoyl-CoA hydratase gene by homologous recombination, or transforming by introducing an autonomously replicating vector having that gene incorporated therein, in the transformant.

[4] The method described in [2] or [3] above, further comprising transforming an ethylmalonyl-CoA decarboxylase gene by homologous recombination, or transforming by introducing an autonomously replicating vector having that gene incorporated therein, in the transformant.

[5] The method described in any of [1] to [4] above, wherein the *C. necator* is strain JMP134 (DSM4058) or strain H16 (DSM428).

[6] The method described in any of [1] to [5] above, wherein the recombinant *C. necator* strain is strain MF01, strain NSDG or strain NSDGΔΔ.

[7] The method described in any of [1] to [6] above, wherein the crotonyl-CoA reductase gene is derived from the actinomycete, *Streptomyces cinnamonensis*.

[8] The method described in [7] above, wherein the crotonyl-CoA reductase gene is composed of:
(a) a nucleic acid containing the base sequence represented by SEQ ID NO: 1, or
(b) a nucleic acid that hybridizes under stringent conditions with a nucleic acid containing the base sequence represented by SEQ ID NO: 1 and encodes a protein having catalytic activity that forms butyryl-CoA from crotonyl-CoA.

[9] The method described in any of [1] to [6] above, wherein the crotonyl-CoA reductase gene is derived from the methanol-assimilating bacterium, *Methylobacterium extorquens*.

[10] The method described in [9] above, wherein the crotonyl-CoA reductase gene is composed of:
(a) a nucleic acid containing the base sequence represented by SEQ ID NO: 2, or
(b) a nucleic acid that hybridizes under stringent conditions with a nucleic acid containing the base sequence represented by SEQ ID NO: 2 and encodes a protein having catalytic activity that forms butyryl-CoA from crotonyl-CoA.

[11] The method described in any of [1] to [10] above, wherein the (R)-specific enoyl-CoA hydratase gene is derived from *C. necator*, and is composed of:
(a) a nucleic acid containing the base sequence represented by SEQ ID NO: 3, or
(b) a nucleic acid that hybridizes under stringent conditions with a nucleic acid containing the base sequence represented by SEQ ID NO: 3 and encodes a protein having activity that converts an intermediate in the fatty acid β-oxidation pathway in the form of 2-enoyl-CoA to (R)-3-hydroxyacyl-CoA.

[12] The method described in [11] above, wherein the ethylmalonyl-CoA decarboxylase gene is composed of:
(a) a nucleic acid containing the base sequence represented by SEQ ID NO: 4, or
(b) a nucleic acid that hybridizes under stringent conditions with a nucleic acid containing the base sequence represented by SEQ ID NO: 4 and encodes a protein having catalytic activity that forms butyryl-CoA by decarboxylation of ethylmalonyl-CoA.

Effects of the Invention

A method can be provided for enhancing the production of P(3HB-co-3HHx) and enhancing the fraction of 3HHx using a saccharide or glycerol as a starting raw material by constructing a novel metabolic pathway in *C. necator* for forming a 3HB unit and a 3HHx unit from acetyl-CoA by genetic manipulation.

BEST MODE FOR CARRYING OUT THE INVENTION

Figure 1:
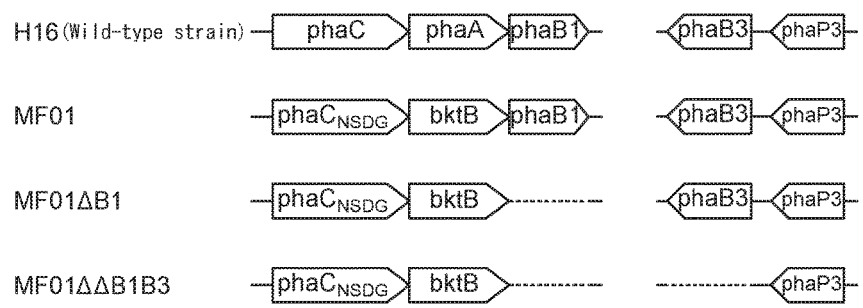
FIG. 1 shows a schematic diagram of the genotypes of *C. necator* strain H16 (wild-type strain), strain MF01, strain MF01ΔB1 and strain MF01ΔΔB1B3.

The following provides a detailed description of preferable embodiments for explaining the present invention.

As was previously described, the inventors of the present invention succeeded in solving the aforementioned problems by exploiting a novel metabolic pathway for forming and copolymerizing a 3HB unit and a 3HHx unit from acetyl-CoA using a wide range of saccharides or glycerol as starting raw materials instead of conventional vegetable oil. More specifically, the present invention relates to a method for producing poly(3-hydroxybutyrate-co-3-hydroxyhexanote), comprising: transforming a recombinant *Cupriavidus necator* strain imparted with the ability to produce poly(3-hydroxybutyrate-co-3-hydroxyhexanoate) by homologous recombination of crotonyl-CoA reductase gene, (R)-specific enoyl-CoA hydratase gene and ethylmalonyl-CoA decarboxylase gene in a chromosome thereof, or transforming by introducing an autonomously replicating vector having these genes incorporated in that strain, and cultivating the transformant in a medium containing a saccharide and/or glycerol as a carbon source, and to a method for enhancing the amount of the copolymer produced and/or enhancing the fraction of the 3HHx unit in the copolymer. Furthermore, the crotonyl-CoA reductase gene, (R)-specific enoyl-CoA hydratase gene and ethylmalonyl-CoA decarboxylase gene referred to here are either all transformed by homologous recombination or are all transformed by introducing these genes into the aforementioned strain in the form of an autonomously replicating vector, or one or two of the crotonyl-CoA reductase gene, (R)-specific enoyl-CoA hydratase gene and ethylmalonyl-CoA decarboxylase gene are transformed by homologous recombination and the remaining gene(s) are transformed by introducing into the aforementioned strain in the form of an autonomously replicating vector. Moreover, in the present aspect, a gene encoding acetoacetyl-CoA reductase may be deficient in a chromosome of the *C. necator* strain.

In a different aspect, the present invention relates to a method for producing poly(3-hydroxybutyrate-co-3-hydroxyhexanote), comprising: transforming a recombinant strain deficient in a gene encoding acetoacetyl-CoA reductase in a chromosome of *Cupriavidus necator* strain imparted with the ability to produce poly(3-hydroxybutyrate-co-3-hydroxyhexanoate in a chromosome thereof, or transforming by introducing an autonomously replicating vector having this gene incorporated in that strain, and cultivating the transformant in a medium containing a saccharide and/or glycerol as a carbon source, or a method for enhancing the amount of the copolymer produced and/or enhancing the fraction of the 3HHx unit in the copolymer. In one aspect thereof, the transformant used in the aforementioned production method may be transformed by homologous recombination of an (R)-specific enoyl-CoA hydratase gene or may be transformed by introducing a autonomously replicating vector having that gene incorporated therein. Moreover, the recombinant used in the aforementioned production method may also be transformed by homologous recombination of ethylmalonyl-CoA decarboxylase gene or (R)-specific enoyl-CoA reductase hydratase gene and ethylmalonyl-CoA decarboxylase gene, or may be transformed by introducing an autonomously replicating vector having those genes incorporated therein.

(1) Host (Microorganism)

The host used in the production method of the present invention is a PHA-producing bacterium in the form of *C. necator*. There are no particular limitations on the *C. necator* used in the production method of the present invention, and examples thereof include strain JMP134 (DSM4058) and strain H16 (DSM428). More specifically, in the present invention, recombinant *C. necator* imparted with the ability to produce P(3HB-co-3HHx) is used preferably, and for example, strain NSDG, strain MF01 or strain NSDGΔA may be used.

When used in the present description, "strain NSDG" refers to a recombinant strain obtained by substituting PHA polymerase gene phaC inherently present in the pha operon in a chromosome of a wild-type strain *C. necator* in the form of strain H16 (ATCC strain 16699 or strain DSM428) with a gene of a mutant of PHA polymerase derived from *A. caviae* in the form of phaC$_{NSDG}$ by homologous recombination (see International Publication No. WO 2011/105379). Here, "phaC$_{NSDG}$" refers to a gene encoding a mutant in which asparagine at position 149 is substituted with serine and aspartic acid at position 71 is substituted with glycine in PHA polymerase derived from an *A. caviae* strain (phaC$_{Ac}$). Furthermore, phaC$_{NSDG}$ gene can be cloned using an ordinary molecular biological technique. In addition, when used in the present description, "strain MF01" refers to a transformant in which phaA of the aforementioned strain NSDG is substituted with β-ketothiolase gene bktB having broad substrate specificity. In addition, "NSDGΔA" refers to a transformant that is deficient in a β-ketothiolase gene in the form of phaA in the aforementioned strain NSDG. The aforementioned three types of H16 mutants can be produced using common genetic engineering techniques based on sequence data of a gene encoding PHA polymerase of *C. necator* (see, for example, Japanese Unexamined Patent Publication No. 2008-29218 and International Publication No. WO 2011/105379).

(2) Gene Encoding Crotonyl-CoA Reductase (Ccr)

According to the present invention, in order to enhance the produced amount of P(3HB-co-3HHx) and/or enhance the fraction of 3HHx, it is necessary to introduce a gene encoding crotonyl-CoA reductase (ccr) into a recombinant *C. necator* strain imparted with the ability to produce that polymer by transformation. Here, "crotonyl-CoA reductase" as used in the present description refers to an enzyme that reduces an intermediate of the fatty acid β-oxidation pathway in the form of crotonyl-CoA having four carbon atoms to form butyryl-CoA serving as the substrate of β-ketothiolase (BktB). (R)-3HHx-CoA having six carbon atoms is supplied by butyryl-CoA condensing with another molecule of acetyl-CoA due to the action of β-ketothiolase and undergoing further conversion, and is then copolymerized with (R)-3HB-CoA by a PHA polymerase having broad substrate specificity. There are no particular limitations on the origin of the biological species of the ccr able to be used in the present invention provided the reductase has the aforementioned activity following translation, and a gene encoding crotonyl-CoA reductase derived from the actinomycete, *S. cinnamonensis* (referred to as "ccr$_{Sc}$") or a gene encoding crotonyl-CoA reductase derived from the methanol-assimilating bacterium, *M. extorquens* (referred to as "ccr$_{Me}$") is used preferably.

Furthermore, the ccr used in the present invention includes single-stranded or double-stranded DNA and an RNA complement thereof. DNA includes, for example, naturally-derived DNA, recombinant DNA, chemically synthesized DNA, DNA amplified by PCR and combinations thereof. DNA is preferably used for the nucleic acid used in the present invention. Furthermore, as is commonly known, codons have degeneracy, and although there are amino acids for which a plurality of base sequences are present that encode a single amino acid, a nucleic acid having any of these base sequences is included in the scope of the present invention provided it is a nucleic acid of a base sequence that encodes crotonyl-CoA reductase.

In one embodiment of the present invention, the base sequence of ccr$_{Sc}$ (GenBank Accession No. AF178673) and the base sequence of ccr$_{Me}$ (NCBI-Gene ID: 7990208), for example, can be used for the ccr used in the present invention. Isolation and identification of ccr can be carried out using an ordinary molecular biological technique. As is described in Example 1 to be subsequently described, for example, these genes can be amplified using genomic DNA as a template and designing synthetic oligonucleotides as primers based on the base sequence of SEQ ID NO: 1 (corresponding amino acid sequence SEQ ID NO: 37) or 2 (corresponding amino acid sequence SEQ ID NO: 38). Furthermore, as is indicated in Example 1, since approximately 1.3 kbp DNA fragments are obtained in the form of PCR fragments with respect to ccr$_{Sc}$ in the case of using the primers of SEQ ID NO: 11 and 12, these fragments can be separated by method in which the DNA fragments are selected according to molecular weight by agarose gel electrophoresis and the like followed by isolation of nucleic acids in accordance with ordinary methods such as by cutting out specific bands. On the other hand, ccr$_{Me}$ can be isolated in the same manner using the primers of SEQ ID NO: 13 and 14.

Here, examples of methods that can be used to amplify nucleic acid include, but are not limited to, reactions requiring temperature cycling such as polymerase chain reaction (PCR) (Saiki, R. K., et al., Science, 230: 1350-1354 (1985)), ligase chain reaction (LCR) (Wu, D. Y., et al., Genomics, 4: 560-569 (1989)) or amplification based on transcription (Kwoh, D. Y., et al., Proc. Natl. Acad. Sci. USA, 86: 1173-1177 (1989)), and constant temperature reactions such as strand displacement amplification (SDA) (Walker, G. T., et al., Proc. Natl. Acad. Sci. USA, 89: 392-396 (1992), Walker, G. T., et al., Nuc. Acids Res., 20: 1691-1696 (1992)), self-sustained sequence replication (3SR) (Guatelli, J. C., et al., Proc. Natl. Acad. Sci. USA, 87: 1874-1878 (1990)) or the Qβ replicase system (Lizardi, P. M., et al., Biotechnology, 6: 1197-1202 (1988)). The PCR method is used preferably in the production method of the present invention.

In one embodiment of the present invention, ccr may be derived from *S. cinnamonensis* and may be composed of (a)

a nucleic acid containing the base sequence represented by SEQ ID NO: 1, or (b) a nucleic acid that hybridizes under stringent conditions with a nucleic acid containing the base sequence represented by SEQ ID NO: 1 and encodes a protein having catalytic activity that forms butyryl-CoA from crotonyl-CoA. In another embodiment of the present invention, ccr may be derived from *M. extorquens* and may be composed of (a) a nucleic acid containing the base sequence represented by SEQ ID NO: 2, or (b) a nucleic acid that hybridizes under stringent conditions with a nucleic acid containing the base sequence represented by SEQ ID NO: 2 and encodes a protein having catalytic activity that forms butyryl-CoA from crotonyl-CoA.

In the present invention, "under stringent conditions" refers to hybridizing under moderately to highly stringent conditions. More specifically, moderately stringent conditions make it possible for person with ordinary skill in the art to easily make a determination based on DNA length, for example. Although basic conditions are indicated in Sambrook, J., et al., Molecular Cloning: A Laboratory Manual (3rd edition), Cold Spring Harbor Laboratory, 7.42-7.45 (2001), with respect to the use of a nitrocellulose filter, hybridization conditions consisting of 5×SSC, 0.5% SDS, prewashing solution of 1.0 mM EDTA (pH 8.0), approximately 50% formamide at about 40° C. to 50° C. and 2×SSC to 6×SSC (or other similar hybridization solution such as Stark's solution in approximately 50% formamide at about 42° C.), and the use of washing conditions consisting of 0.5×SSC and 0.1% SDS at about 60° C. are included. Highly stringent conditions also enable a person with ordinary skill in the art to easily make a determination based on DNA length, for example. In general, such conditions include hybridization and/or washing at a higher temperature and/or lower temperature than that used for moderately stringent conditions, and are defined as, for example, the aforementioned hybridization conditions accompanied by washing at 0.2×SSC and 0.1% SDS at about 68° C. A person with ordinary skill in the art would have the awareness to be able to suitably adjust temperature and salt concentration of the washing solution as necessary corresponding to such factors as the length of the probe.

Homologous nucleic acids cloned by using nucleic acid amplification or hybridization as previously described respectively have identity of at least 30% or more, preferably 50% or more, more preferably 70% or more, even more preferably 90% or more, still more preferably 95% or more, and most preferably 98% or more based on the base sequence set forth in SEQ ID NO: 1 or 2. Furthermore, percent identity can be determined by visual examination or mathematical calculation. Alternatively, the percent identity of two nucleic acid sequences is described in Devereux, J., et al., Nucl. Acids Res., 12: 387 (1984), and can be determined by comparing sequence data using a GAP computer program (GCG Wisconsin Package, Version 10.3) available from the University of Wisconsin Genetics Computer Group (UWGCG).

In a more preferable aspect of the present invention, the ccr introduced into the host is $ccr_{Sc}$ or $ccr_{Me}$, and may be a nucleic acid composed of the base sequence represented by SEQ ID NO: 1 or 2. Furthermore, as is understood by a person with ordinary skill in the art, in order for a gene introduced into a chromosome of a host to be suitably transcribed and further translated into a protein having a desired activity, it is necessary for the gene to be incorporated so as to be under the control of a suitable promoter in the chromosome. Furthermore, a promoter of a different species from the host may also be suitably used by introducing into a chromosome by a genetic engineering procedure instead of using a promoter unique to the host chromosome.

(3) Gene Encoding (R)-Specific Enoyl-CoA Hydratase (phaJ)

In the copolymer production method according to the present invention, a gene encoding (R)-specific enoyl-CoA hydratase (phaJ) may be further introduced into a host introduced with the aforementioned gene encoding crotonyl-CoA reductase. Here, the "(R)-specific enoyl-CoA hydratase" used in the present invention refers to an enzyme that converts a fatty acid β-oxidation-based intermediate in the form of 2-enoyl-CoA to a PHA monomer in the form of (R)-3-hydroxyacyl-CoA, and although there are no particular limitations on the origin of the biological species provided it has that activity, it is preferably derived from a strain of *C. necator*.

Furthermore, the phaJ used in the present invention includes single-stranded or double-stranded DNA and an RNA complement thereof. DNA includes, for example, naturally-derived DNA, recombinant DNA, chemically synthesized DNA, DNA amplified by PCR and combinations thereof. DNA is preferably used for the nucleic acid used in the present invention. Furthermore, as is commonly known, codons have degeneracy, and although there are amino acids for which a plurality of base sequences are present that encode a single amino acid, a nucleic acid having any of these base sequences is included in the scope of the present invention provided it is a base sequence of a nucleic acid that encodes (R)-specific enoyl-CoA hydratase.

In one embodiment of the present invention, H16_A1070 derived from *C. necator* (to be referred to as "phaJ4a") (NCBI-Gene ID: 4248689) can be used for the phaJ used in the present invention. Furthermore, isolation and identification of phaJ introduced into a host can be carried out by an ordinary molecular biological technique. Moreover, in one embodiment of the present invention, phaJ may be composed of (a) a nucleic acid containing the base sequence represented by SEQ ID NO: 3, or (b) a nucleic acid that hybridizes under stringent conditions with a nucleic acid containing the base sequence represented by SEQ ID NO: 3 (corresponding amino acid sequence SEQ ID NO: 39) and encodes a protein having activity that converts a fatty acid β-oxidation-based intermediate in the form of enoyl-CoA to (R)-3-hydroxyacyl-CoA. Moreover, in another embodiment of the present invention, phaJ may be composed of (a) a nucleic acid containing the base sequence represented by SEQ ID NO: 3, or (b) a nucleic acid that hybridizes under stringent conditions with a nucleic acid containing the base sequence represented by SEQ ID NO: 3 and encodes a protein having activity that converts a fatty acid β-oxidation-based derivative to (R)-3-hydroxyacyl-CoA.

Furthermore, the meaning of "under stringent conditions" is as was previously described, and homologous nucleic acids cloned by using nucleic acid amplification or hybridization respectively have identity of at least 30% or more, preferably 50% or more, more preferably 70% or more, even more preferably 90% or more, still more preferably 95% or more, and most preferably 98% or more based on the base sequence set forth in SEQ ID NO: 3.

In a more preferable aspect of the present invention, the gene encoding (R)-specific enoyl-CoA hydratase introduced into a host may be phaJ4a and may be a nucleic acid composed of the base sequence represented by SEQ ID NO: 3. Furthermore, as is understood by a person with ordinary skill in the art, in order for a gene introduced into a chromosome of a host to be suitably transcribed and further translated into a protein having a desired activity, it is necessary for the gene to be incorporated so as to be under the control of a suitable promoter. Furthermore, a promoter of a different species from the host may also be suitably used by introducing into a chromosome by a genetic engineering procedure instead of using a promoter unique to the host chromosome.

(4) Ethylmalonyl-CoA Decarboxylase Gene (Emd)

In the copolymer production method according to the present invention, ethylmalonyl-CoA decarboxylase gene (emd) may be introduced into a host introduced with a gene encoding the aforementioned crotonyl-CoA reductase gene in place or in addition to a gene encoding (R)-specific enoyl-CoA hydratase (phaJ). Here, the "ethylmalonyl-CoA decarboxylase" used in the present invention refers to an enzyme that catalyzes a decarboxylation reaction of ethylmalonyl-CoA, which is formed in a side reaction by propionyl-CoA carboxylase in animal cells, to butyryl-CoA, and there are no particular limitations on the source of the biological species provided it has this activity.

Furthermore, the emd used in the present invention includes single-stranded or double-stranded DNA and an RNA complement thereof. DNA includes, for example, naturally-derived DNA, recombinant DNA, chemically synthesized DNA, DNA amplified by PCR and combinations thereof. DNA is preferably used for the nucleic acid used in the present invention. Furthermore, as is commonly known, codons have degeneracy, and although there are amino acids for which a plurality of base sequences are present that encode a single amino acid, a nucleic acid having any of these base sequences is included in the scope of the present invention provided it is a base sequence of a nucleic acid that encodes ethylmalonyl-CoA decarboxylase.

In one embodiment of the present invention, a gene that is artificially reverse-translated based on an amino acid sequence (GenBank Accession No. NP_001103665) of ethylmalonyl-CoA decarboxylase derived from mouse (to be referred to as "$emd_{Mm}$"), for example, can be used for the emd used in the present invention. This artificial gene can be acquired by gene synthesis commissioned to various private corporations. Moreover, in one embodiment of the present invention, emd may be composed of (a) a nucleic acid composed of the base sequence represented by SEQ ID NO: 4 (corresponding amino acid sequence SEQ ID NO: 40), or (b) a nucleic acid that hybridizes under stringent conditions with a nucleic acid containing the base sequence represented by SEQ ID NO: 4 and encodes a protein that has catalytic activity that forms butyryl-CoA by decarboxylation of ethylmalonyl-CoA. Moreover, in another embodiment of the present invention, emd may be composed of (a) a nucleic acid composed of a base sequence represented by SEQ ID NO: 4, or (b) a nucleic acid that hybridizes under stringent conditions with a nucleic acid composed of the base sequence represented by SEQ ID NO: 4 and encodes a protein that has catalytic activity that forms butyryl-CoA by decarboxylation of ethylmalonyl-CoA.

Furthermore, the meaning of "under stringent conditions" is as was previously described, and homologous nucleic acids cloned by using nucleic acid amplification or hybridization respectively have identity of at least 30% or more, preferably 50% or more, more preferably 70% or more, even more preferably 90% or more, still more preferably 95% or more, and most preferably 98% or more based on the base sequence set forth in SEQ ID NO: 4.

In a more preferable aspect of the present invention, the ethylmalonyl-CoA decarboxylase gene introduced into a host may be $emd_{Mm}$ and may be a nucleic acid composed of the base sequence represented by SEQ ID NO: 4. Furthermore, as is understood by a person with ordinary skill in the art, in order for a gene introduced into a chromosome of a host to be suitably transcribed and further translated into a protein having a desired activity, it is necessary for the gene to be incorporated so as to be under the control of a suitable promoter. Furthermore, a promoter of a different species from the host may also be suitably used by introducing into a chromosome by a genetic engineering procedure instead of using a promoter unique to the host chromosome.

(5) Gene Encoding Acetoacetyl-CoA Reductase

According to one aspect of the present invention, a recombinant strain of C. necator that is deficient in a gene encoding acetoacetyl-CoA reductase is used preferably. "Acetoacetyl-CoA reductase" refers to an enzyme having a catalytic function that forms (R)-3HB-CoA reductase using acetoacetyl-CoA as substrate, known types thereof for C. necator consist of "PhaB1", "PhaB2" and "PhaB3", and although PhaB1 primarily functions in the aforementioned reaction under growth conditions with fructose, a paralog thereof in the form of PhaB3 has also been reported to function (Budde, C. F., et al., J. Bacteriol., 192: 5319-5328 (2010)). As was described above, a strain deficient in a gene encoding acetoacetyl-CoA reductase is used preferably for the recombinant strain of C. necator used in the production method of one embodiment of the present invention, and the deficient gene encoding acetoacetyl-CoA reductase is preferably phaB1 alone or phaB1 and phaB3, and more preferably phaB1 alone. Here, the base sequences of the deficient genes (phaB1 and phaB3) are known, and can be used to obtain a recombinant C. necator in which either or both of these genes are deficient by referring to, for example, NCBI-Gene ID: 4249874 and NCBI-Gene ID: 4250155, respectively. When used in the present description, "deficient" refers to a state in which all or a portion of a target gene is no longer present due to genetic manipulation, and results in the loss of all or a portion of the activity of the protein encoded by that gene. Furthermore, deficiency mutations can be induced using a known site-specific mutagenesis method (Current Protocols in Molecular Biology, Vol. 1, Section 8.1.1, 1994) or a commercially available kit (LA PCR In Vitro Mutagenesis Series Kit, Takara).

(6) Construction of Gene Replacement Vector and Production of Recombinant

Microorganisms

According to the present invention, a gene replacement vector obtained by incorporating each of ccr, phaJ and emd or each of their respective combinations in a homologous recombination vector or an expression vector obtained by incorporating each of these genes or their respective combinations in an autonomously replicating vector is provided for introducing these genes into a chromosome of a host. Here, an example of a method used to incorporate a gene into a vector includes that method described in Sambrook J., et al., Molecular Cloning: A Laboratory Manual (3rd edition), Cold Spring Harbor Laboratory, 1.1 (2001). A commercially available ligation kit (such as that manufactured by Toyobo) can also be used for convenience.

The vector can be easily prepared by linking a desired gene to a recombination vector available in the art (such as plasmid DNA) by an ordinary method. Although there are no particular limitations on the vector used in the method for controlling the polyhydroxyalkanoate copolymer of the present invention provided it is used for the purpose of replacing a polyester polymerase gene of microbial origin already incorporated in a chromosome of a microorganism with a foreign polyester polymerase gene having broad substrate specificity within a microorganism, the homologous recombination vector pK18mobsacB (Schafer, A., et al., Gene, 145: 69-73 (1994)) or pJQ200 (Quandt, J. and Hynes, M. P., "Versatile suicide vectors for gene replacement in gram-negative bacteria", Gene (1993), 127: 15-21) is used preferably. Alternatively, other examples include, but are not limited to, wide-host-range vectors known to replicate autonomously in gram-negative bacteria, consisting of pBBR1-MCS2 (GenBank Accession No. U23751), pJRD215 (M16198) (refer to Davison, J., et al., Gene, 51: 275-280 (1987)), pJB861 (U82000) and pHRP311 (refer to Parales, R. E. & Harwood, C. S., Gene, 133: 23-30 (1993)). In addition, examples of *Escherichia coli* plasmids that can be used include pBAD24 (GenBank Accession No. X81837), pDONR201, pBluescript, pUC118, pUC18, pUC19 and pBR322.

In addition, a person with ordinary skill in the art would be able to suitably select restriction ends so as to accommodate the recombination vector, as well as suitably select a recombination vector suitable for host cells in order to express a desired protein. Such vectors are constructed or preferably constructed so that a region functioning so as to induce homologous recombination of a gene used in the present invention with a target gene of a host cell (such as a self-replication origin, conjugal transfer region or selection marker (such as a kanamycin resistance gene)) is suitably arranged or introduced therein.

In general, a transformant can be produced by incorporating a recombination vector in host cells. In this case, prokaryotic cells (such as *E. coli* (e.g. strain S17-1) or *Bacillus subtilis*) or eukaryotic cells (such as mammalian cells, yeast or insect cells) can be used for the host cells. The recombination vector can be introduced into host cells (transformation) using a known method. Examples thereof in the case of bacteria (such as *E. coli* or *B. subtilis*) include the method of Cohen (Proc. Natl. Acad. Sci. USA, 69: 2110 (1972)), the protoplast method (Mol. Gen. Genet., 168: 111 (1979)), the competent method (J. Mol. Biol., 56: 209 (1971), the calcium chloride method and electroporation. In addition, conjugal transfer (J. Bacteriol., 147: 198 (1981)) can be used to introduce cells belonging to the genus *Ralstonia*, the genus *Alcaligenes* or the genus *Pseudomonas* into an expression vector.

Conjugal transfer utilizes the property of bacteria of causing a chromosomal genome to transfer from one cell to another cell as a result of contact between cells, and is a means for enabling gene insertion by a series of steps that begins with bacterial conjugation between a donor organism having an autonomously replicating plasmid carrying target DNA and an acceptor organism that does not have that plasmid, and continue with formation of a bridge between both organisms, replication and migration of the plasmid, and completion of DNA synthesis together with separation of the bacterial cells.

(7) Synthesis of P(3HB-Co-3HHx) Copolymer

According to the present invention, synthesis of P(3HB-co-3HHx) copolymer is carried out by introducing crotonyl-CoA reductase gene, (R)-specific enoyl-CoA hydratase gene and ethylmalonyl-CoA decarboxylase gene into a chromosome of a recombinant *C. necator* strain imparted with the ability to produce the copolymer, or introduce crotonyl-CoA reductase gene into a chromosome of a recombinant strain deficient in a gene encoding acetoacetyl-CoA reductase of a recombinant *C. necator* strain imparted with the ability of produce the copolymer, and then forming and accumulating the copolymer in the recombinant strain or culture thereof (such as a medium) by introducing (R)-specific enoyl-CoA hydratase gene or ethylmalonyl-CoA decarboxylase gene followed by harvesting the target polymer from the recombinant strain or culture. Furthermore, as is understood by a person with ordinary skill in the art, it is preferable to place the aforementioned recombinant strain under suitable culturing conditions for synthesizing the polymer. These culturing conditions may be in accordance with the culturing conditions of the parent strain prior to carrying out this culturing of the recombinant strain and gene recombination. In addition, in a specific embodiment of the present invention, a recombinant strain may be cultivated in medium containing a saccharide and/or glycerol for the carbon source.

An example of a medium in the case of using a recombinant *C. necator* strain for the host consists of a medium obtained by adding a saccharide or glycerol able to be assimilated by the microorganism followed by limiting the nitrogen source, inorganic salt or other organic nutrient sources. Typically, by aerobically culturing for 1 day to 10 days within a temperature range of the medium of 25° C. to 37° C., the polymer can be made to accumulate in the bacterial cells, after which the desired copolymer can be obtained by recovery and purification. In addition, a common, commercially available saccharide can be used for the saccharide able to be used in the present invention, and there are no particular limitations on the supply source thereof. A "saccharide" refers to a polyvalent alcohol having an aldehyde group or ketone group, and includes monosaccharides, oligosaccharides, polysaccharides and saccharide derivatives. Specific examples of monosaccharides include glucose, galactose, mannose, glucosamine, N-acetylglucosamine and fructose. Specific examples of disaccharides include maltose, isomaltose, lactose, lactosamine, N-acetyl-lactosamine, cellobiose and melibiose. Specific examples of oligosaccharides include homooligomers composed of glucose, galactose, mannose, glucosamine, N-acetylglucosamine or fructose, and heterooligomers composed of two or more components such as glucose, galactose, mannose, glucosamine, N-acetylglucosamine, fructose or sialic acid, and examples thereof include maltooligosaccharides, isomaltooligosaccharides, lactooligosaccharides, lactosamine oligosaccharides, N-acetyllactosamine oligosaccharides, cellooligosaccharides or melibiooligosaccharides. Examples of polysaccharides include those found in a wide range of organisms, such as animals, plants (including kelp), insects and microorganisms. Examples thereof include N-linked sugar chains, O-linked sugar chains, glycosaminoglycans, starch, amylose, amylopectin, cellulose, chitin, glycogen, agarose, alginic acid, hyaluronic acid, inulin and glucomannan. Examples of saccharide derivatives include deoxyribose ($C_5H_{10}O_4$) and sulfated polysaccharides. Furthermore, although the concentration of saccharide in the medium is preferably 0.1% to 5%, it can be suitably adjusted by a person with ordinary skill in the art.

"Glycerol" is frequently interchangeably used with the term "glycerin". However, more appropriately, "glycerol" applies to a highly chemically pure compound in the form of 1,2,3-propanetriol, while "glycerin" applies to commercial products in which the glycerol content has typically been purified to 95% or more. According to the present invention, either may be used in the case of using as a carbon source. Furthermore, although glycerol or glycerin concentration in the medium is preferably 0.1% to 5%, it can be suitably adjusted by a person with ordinary skill in the art. In addition, the present invention does not exclude an aspect in which a saccharide and glycerol (glycerin) are mixed for use as the carbon source.

In addition, a nitrogen source or mineral may also be added to the medium as necessary. Examples of nitrogen sources include ammonia, ammonium salts such as ammonium chloride, ammonium sulfate or ammonium phosphate, peptones, beef extract, yeast extract and corn steep liquor. Examples of minerals include monocalcium phosphate, dicalcium phosphate, magnesium phosphate, magnesium sulfate and sodium chloride.

Shake culturing is normally used for culturing, and is preferably carried out for at least one day following induction of gene expression under aerobic conditions at 25° C. to 37° C. Antibiotics such as kanamycin or ampicillin may be added to the medium. In addition, gene expression inducers such as arabinose, indole acrylic acid (IAA) or isopropyl-β-D-thiogalactopyranoside (IPTG) can be used as necessary. A person with ordinary skill in the art would be able to suitably select applicable culturing conditions and conditions for inducing gene expression in order to express the desired gene.

(8) Purification and Structural Analysis of P(3HB-Co-3HHx)

In the present invention, the copolymer can be purified as indicated below. The transformant is recovered from the medium by centrifugal separation and then washed with distilled water followed by drying or freeze-drying. Subsequently, after drying with chloroform, the transformant is suspended and stirred for a prescribed amount of time at room temperature to extract the copolymer. The suspension of the transformant may be heated during the extraction stage. The residue is removed by filtration and methanol is added to the supernatant to precipitate the copolymer, followed by subjecting the precipitate to filtration or centrifugal separation to remove the supernatant and drying to obtain the purified polymer. Subsequently, although not limited thereto, the composition ratio of monomer units in the resulting copolymer can be confirmed using nuclear magnetic resonance (NMR) or gas chromatography.

In one aspect of the present invention, the fraction of 3HHx in the P(3HB-co-3HHx) is at least 1 mol % and may be, for example, 1 mol %, 2 mol %, 3 mol %, 4 mol %, 5 mol %, 6 mol %, 7 mol %, 8 mol %, 9 mol % or 10 mol % or more. In addition, the fraction of 3HHx may be 99 mol % or less, and may be, for example, 99 mol %, 98 mol %, 97 mol %, 96 mol %, 95 mol %, 94 mol %, 93 mol %, 92 mol %, 91 mol % or 90 mol % or less. Although there are no particular limitations thereon, examples of possible ranges of the fraction of 3HHx include 1 mol % to 99 mol %, 1 mol % to 95 mol %, 1 mol % to 90 mol %, 1 mol % to 85 mol %, 1 mol % to 80 mol %, 1 mol % to 75 mol %, 1 mol % to 70 mol %, 1 mol % to 65 mol %, 1 mol % to 60 mol %, 1 mol % to 55 mol %, 1 mol % to 50 mol %, 1 mol % to 45 mol %, 1 mol % to 40 mol %, 1 mol % to 35 mol %, 1 mol % to 30 mol %, 1 mol % to 25 mol %, 1 mol % to 20 mol %, 2 mol % to 99 mol %, 2 mol % to 95 mol %, 2 mol % to 90 mol %, 2 mol % to 85 mol %, 2 mol % to 80 mol %, 2 mol % to 75 mol %, 2 mol % to 70 mol %, 2 mol % to 65 mol %, 2 mol % to 60 mol %, 2 mol % to 55 mol %, 2 mol % to 50 mol %, 2 mol % to 45 mol %, 2 mol % to 40 mol %, 2 mol % to 35 mol %, 2 mol % to 30 mol %, 2 mol % to 25 mol %, 2 mol % to 20 mol %, 3 mol % to 99 mol %, 3 mol % to 95 mol %, 3 mol % to 90 mol %, 3 mol % to 85 mol %, 3 mol % to 80 mol %, 3 mol % to 75 mol %, 3 mol % to 70 mol %, 3 mol % to 65 mol %, 3 mol % to 60 mol %, 3 mol % to 55 mol %, 3 mol % to 50 mol %, 3 mol % to 45 mol %, 3 mol % to 40 mol %, 3 mol % to 35 mol %, 3 mol % to 30 mol %, 3 mol % to 25 mol %, 3 mol % to 20 mol %, 4 mol % to 99 mol %, 4 mol % to 95 mol %, 4 mol % to 90 mol %, 4 mol % to 85 mol %, 4 mol % to 80 mol %, 4 mol % to 75 mol %, 4 mol % to 70 mol %, 4 mol % to 65 mol %, 4 mol % to 60 mol %, 4 mol % to 55 mol %, 4 mol % to 50 mol %, 4 mol % to 45 mol %, 4 mol % to 40 mol %, 4 mol % to 35 mol %, 4 mol % to 30 mol %, 4 mol % to 25 mol %, 4 mol % to 20 mol %, 5 mol % to 99 mol %, 5 mol % to 95 mol %, 5 mol % to 90 mol %, 5 mol % to 85 mol %, 5 mol % to 80 mol %, 5 mol % to 75 mol %, 5 mol % to 70 mol %, 5 mol % to 65 mol %, 5 mol % to 60 mol %, 5 mol % to 55 mol %, 5 mol % to 50 mol %, 5 mol % to 45 mol %, 5 mol % to 40 mol %, 5 mol % to 35 mol %, 5 mol % to 30 mol %, 5 mol % to 25 mol % and 5 mol % to 20 mol %. The fraction of 3HHx is preferably 3 mol % to 90 mol %, more preferably 4 mol % to 80 mol % and even more preferably 5 mol % to 70 mol %. Here, when used in the present description, the term "mol %" refers to the result of dividing the number of moles of a certain component by the sum of the number of moles of each component in a multicomponent system. In addition, the copolymer obtained according to the control method of the present invention is accumulated in microorganisms at the rate of 20% by weight to 95% by weight, and preferably 40% by weight to 95% by weight, based on the dry weight of the microorganisms.

EXAMPLES

The following provides a more detailed explanation of the present invention based on examples thereof. The present invention is naturally not limited to the following examples.

Example 1: Study of C. Necator Strain Used as Host and Crotonyl-CoA Reductase (1) Host A wild-type strain of C. necator in the form of strain H16 has a phaCAB1 operon in a chromosome thereof that encodes PHA polymerase (PhaC), β-ketothiolase (PhaA) and acetoacetyl-CoA reductase (PhaB1) establishing the biosynthesis pathway of P(3HB). The previously prepared C. necator strain MF01 is a recombinant strain in which phaC in the phaCAB1 operon of strain H16 is substituted with a mutant gene phaC$_{NSDG}$ of PHA polymerase derived from A. caviae strain, and phaA is substituted with gene bktB of β-ketothiolase having broad substrate specificity derived from C. necator (FIG. 1), and is able to biosynthesize P(3HB-co-3HHx) containing 2.6 mol % of a 3HHx unit by using soybean oil as a carbon source (International Publication No. WO 2011/105379, Mifune, J., et al., Polym. Degrad. Stab., 95: 1305-1312 (2010)). These strains were used to study the produced amount of P(3HB-co-3HHx) and the fraction of 3HHx. Furthermore, in the following examples, PCR was basically carried out using KOD Plus DNA Polymerase (Toyobo) for 30 cycles, with one cycle consisting of reacting for 20 seconds at 98° C., 20 seconds at 60° C. and 2 minutes 30 seconds at 68° C., and the temperature conditions were suitably adjusted as necessary.

(2) Construction of Plasmid Vector for Deletion of Acetoacetyl-CoA Reductase Gene phaB1

Homologous recombination plasmid pK18msbktBR for deleting a gene (phaB1) that encods acetoacetyl-CoA reductase PhaB1 in a chromosome of C. necator strain MF01 was constructed in the manner indicated below. First, β-ketothiolase gene (bktB) derived from C. necator was amplified by PCR using genomic DNA of C. necator strain H16 as a template and using oligonucleotides of Sequence 1 and Sequence 2 indicated below as primers.

```
Sequence 1:
                                     (SEQ ID NO: 5)
TACATGGATCCAAGGGAGGCAAAGTCATGACGCGTGAA
GTGGTAGTG Sequence 2:
                                     (SEQ ID NO: 6)
GGATCATATGCTTCCTCAGATACGCTCGAAGATGGC
```

The amplified bktB fragment was treated with restriction enzymes BamHI and NdeI. The restricted fragment was ligated with a fragment obtained by treating a previously constructed homologous recombination plasmid pK18msNSDG-R (containing a DNA fragment obtained by ligating phaC$_{NSDG}$ and a downstream region of phaB1) (Mifune, J., et al., Polym. Degrad. Stab., 95: 1305-1312 (2010)) with the same restriction enzyme BamHI and NdeI, to obtain phaB1 deletion plasmid pK18msbktBR.

(3) Construction of Plasmid Vector for Deletion of Acetoacetyl-CoA Reductase Gene phaB3

Homologous recombination plasmid pK18msΔphaB3 for deleting a gene (phaB3) that encodes acetoacetyl-CoA reductase PhaB3 in a chromosome of C. necator strain MF01 was constructed in the manner indicated below. First, the upstream and downstream regions of phaB3 derived from C. necator were respectively amplified by PCR using genomic DNA of C. necator strain H16 as a template and using the oligonucleotides of Sequence 3 and Sequence 4, and Sequence 5 and Sequence 6, indicated below as primers.

```
Sequence 3:
                                     (SEQ ID NO: 7)
TTTGGAATTCTACCTAGGGATCAAATTAGAGGAAA Sequence 4:
                                     (SEQ ID NO: 8)
CCTTACTGCATGTGCCTGCTTCATTCTCGTAAAGTTGAAAG Sequence 5:
                                     (SEQ ID NO: 9)
GAATGAAGCAGGCACATGCAGTAAGGGTGCTGGG Sequence 6:
                                     (SEQ ID NO: 10)
TCCTAAGCTTGCTGACCGTGATCGTCGACAACTTTGAAGA
CCTGA
```

Here, an overlap region is added in Sequence 4 and Sequence 5. Next, the amplified phaB3 upstream fragment and downstream fragment were purified and mixed, and a fragment obtained by linking the upstream and downstream regions of phaB3 was amplified by fusion PCR using the oligonucleotides of Sequence 3 and Sequence 6 as primers. The amplified fragment linking the upstream and downstream fragments of phaB3 was treated with EcoRI and HindIII. This restricted fragment was then ligated with vector plasmid pK18mobsacB treated with EcoRI and HindIII to obtain phaB3 deletion plasmid pK18msΔphaB3.

(4) Transformation of C. Necator Strain MF01 by Conjugal Transfer and Homologous Recombination Recombination plasmid pK18msbktBR obtained in section (2) of Example 1 and deletion plasmid pK18 msΔphaB3 obtained in section (3) were introduced into C. necator strain MF01 by conjugal transfer to acquire a strain in which genes had been disrupted by homologous recombination. First, the prepared vectors were introduced into E. coli strain S17-1 using the calcium chloride method. Next, this recombinant E. coli was cultured overnight at 37° C. in 30 ml of LB medium (1% tryptone, 1% sodium chloride, 0.5% yeast extract, pH 7.2). In parallel therewith, C. necator strain MF01 was cultured overnight at 30° C. in 3.0 ml of NR medium (1% beef and fish extract, 1% polypeptone, 0.2% yeast extract). Subsequently, 0.1 ml of the culture broth of C. necator strain MF01 was mixed with 0.2 ml of the E. coli culture broth followed by culturing for 6 hours at 30° C. This bacterial cell mixture was coated onto Simmons citrate agar medium containing 0.2 mg/ml of kanamycin (Difco) followed by culturing for 3 days at 30° C. Since the C. necator cells into which the plasmid was transferred from recombinant E. coli cells was transferred and inserted into the chromosome by homologous recombination exhibit kanamycin resistance, while the recombinant E. coli is unable to grow on Simmons citrate agar medium, the colonies that grew on the aforementioned medium are the C. necator transformant (pop-in strain) generated by homologous recombination between the chromosome and vector. Then, the pop-in strain was cultured overnight at 30° C. in NR medium followed by inncoulating onto NR medium containing 10% sucrose and culturing for 3 days at 30° C. The levansucrase encoded by sacB in the vector derived from pK18mobsacB accumulates toxic polysaccharides within cells using sucrose as a substrate. Consequently, only the strain from which the plasmid region has been excised (pop-out strain) is able to grow on the medium containing 10% sucrose. Those strains in which homologous recombination occurred at the target site of a chromosome were selected from these colonies by PCR. Strain MF01ΔB1 deficient in phaB1 was acquired by transforming strain MF01 using pk18msbktBR, while strain MF01ΔB3 deficient in phaB3 was acquired by transforming strain MF01 using pk18 msΔphaB3. Moreover, strain MF01ΔΔB1B3 double-deficient in phaB1 and phaB3 was acquired by transforming strain MF01ΔB1 using pK18 msΔphaB3 (FIG. 1).

(5) Construction of Crotonyl-CoA Reductase Gene Ccr Expression Vector

Expression vector pBBR-ccrSc was constructed by inserting crotonyl-CoA reductase gene derived from the actinomycete, S. cinnamonensis (ccr$_{Sc}$) at downstream of the lac promoter in the plasmid pBBR1-MCS2 capable of autonomously replicating in C. necator cells. In addition, expression vector pBBR-ccr$_{Me}$, having crotonyl-CoA reductase gene derived from the methanol-assimilating bacterium, M. extorquens (ccr$_{Me}$) at downstream of the lac promoter in plasmid pBBR1-MCS2, and expression vector pBPP-ccr$_{Me}$, having this gene at downstream of the phaP1 promoter in pBPP, were constructed. The following provides a detailed description thereof.

(i) Construction of pBBR-ccrSc

A region of ccr$_{Sc}$ was amplified by PCR using previously constructed plasmid pJBccrEE32D13 harboring ccr$_{Sc}$ (Fukui, T., et al., Biomacromolecules, 3: 618-624 (2002)) as a template and using the oligonucleotides of Sequence 7 and Sequence 8 indicated below as primers. Here, since ccr$_{Sc}$ (SEQ ID NO: 1) uses GTG as a start codon, the start codon was converted to ATG by PCR using Sequence 7.

Sequence 7:
(SEQ ID NO: 11)
AGCAATTCAGGAGGAACCTGGATGAAGGAAATCCTGGACG

Sequence 8:
(SEQ ID NO: 12)
AGGTCTAGACTGCGTTCAGACGTTGCGGA

The amplified $ccr_{Sc}$ fragment was treated with restriction enzymes EcoRI and XbaI. This restricted fragment was ligated with a fragment obtained by treating pBBR1-MCS2 with the same restriction enzymes EcoRI and XbaI to obtain $ccr_{Sc}$ expression plasmid pBBR-ccrSc.

(ii) Construction of pBBR-Ccr$_{Me}$

A region of $ccr_{Me}$ was amplified by PCR using genomic DNA of *M. extorquens* strain AM1 as a template and using the oligonucleotides of Sequence 9 and Sequence 10 indicated below as primers.

Sequence 9:
(SEQ ID NO: 13)
ACGAATTCAGGAGGAACCTGGATGGCTGCAAGCGCAGCACC

Sequence 10:
(SEQ ID NO: 14)
AGGTCTAGATCACATCGCCTTGAGCGG

The amplified $ccr_{Me}$ fragment was treated with restriction enzymes EcoRI and XbaI. This restricted fragment was ligated with a fragment obtained by treating pBBR1-MCS2 with the same restriction enzymes EcoRI and XbaI to obtain $ccr_{Me}$ expression plasmid pBBR-ccr$_{Me}$.

(iii) Construction of pBPP-Ccr$_{Me}$

A region of $ccr_{Me}$ was amplified using genomic DNA of *M. extorquens* strain AM1 as a template and using the oligonucleotides of Sequence 11 and Sequence 12 indicated below as primers.

Sequence 11:
(SEQ ID NO: 15)
ATACATATGGCTGCAAGCGCAGCACCGGCCT

Sequence 12:
(SEQ ID NO: 16)
TATGAATTCTCACATCGCCTTGAGCGGGCC

Figure 2:
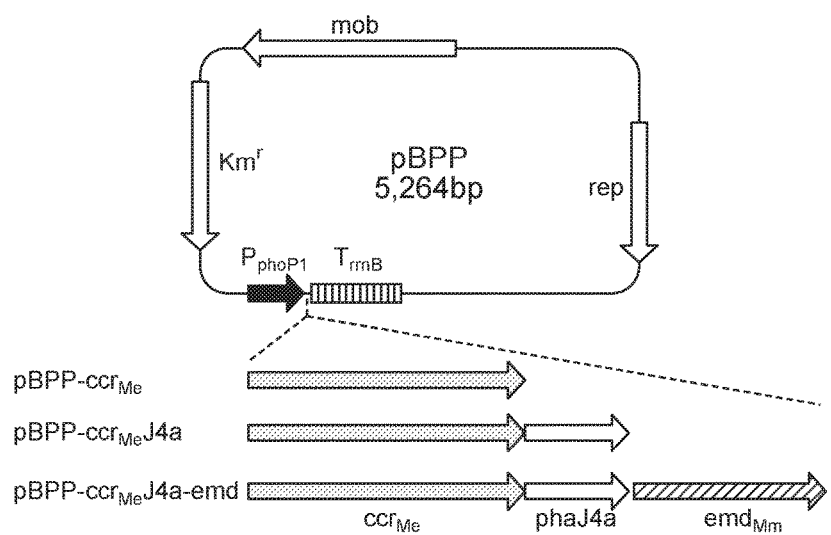
FIG. 2 shows a schematic diagram of vector pBPP-ccr$_{Me}$ expressing crotonyl-CoA reductase gene ccr$_{Me}$, vector pBPP-ccr$_{Me}$J4a co-expressing ccr$_{Me}$ and (R)-specific enoyl-CoA hydratase gene phaJ4a, and vector pBPP-ccr$_{Me}$J4a-emd co-expressing ccr$_{Me}$, phaJ4a and ethylmalonyl-CoA decarboxylase gene emd$_{Mm}$.

The amplified $ccr_{Me}$ fragment was treated with restriction enzymes NdeI and EcoRI. This restricted fragment was ligated with a fragment obtained by treating pBPP with the same restriction enzymes NdeI and EcoRI to obtain $ccr_{Me}$ expression plasmid pBPP-ccr$_{Me}$ (FIG. 2).

(6) Construction of Co-Expression Vector of Crotonyl-CoA Reductase Gene Ccr$_{Me}$ and (R)-Specific Enoyl-CoA Hydratase Gene phaJ4a A region of phaJ4a was amplified by PCR using genomic DNA of *C. necator* strain H16 as a template and using oligonucleotides of Sequence 13 and Sequence 14 indicated below as primers.

Sequence 13:
(SEQ ID NO: 17)
CCCAAGCTTTATCGTCAAGAGGAGACTATCG

Sequence 14:
(SEQ ID NO: 18)
CCCAAGCTTGGATCCTCACCCGTAGCGGCGCGTGAT

The amplified phaJ4a fragment was treated with restriction enzyme HindIII. This restricted fragment was ligated with a fragment obtained by treating pBPP-ccr$_{Me}$ with the same restriction enzyme HindIII to obtain plasmid pBPP-ccr$_{Me}$J4a for co-expression of ccr$_{Me}$ and phaJ4a (FIG. 2).

(7) Construction of Co-Expression Vector of Crotonyl-CoA Reductase Gene Ccr$_{Me}$, (R)-Specific Enoyl-CoA Hydratase Gene phaJ4a and Ethylmalonyl-CoA Decarboxylase Gene Emd$_{Mm}$ First, a plasmid deficient in the region between the EcoRI site and HindIII site on the vector was constructed by digesting pBPP-ccr$_{Me}$J4a with EcoRI and HindIII followed by self-ligation after blunting both the ends. A plasmid pBPP-ccr$_{Me}$J4a-emd for co-expression of ccr$_{Me}$, phaJ4a and emd$_{Mm}$ was obtained by ligating a region of emd$_{Mm}$, obtained from a vector harboring an artificially synthesized emd$_{Mm}$, (synthesis commissioned to Eurofin) by excision with BamHI, with a fragment obtained by treating the aforementioned pBPP-ccr$^{Me}$J4a-modified vector with BamHI (FIG. 2).

(8) Biosynthesis of PHA from Fructose Raw Material

When recombinant MF01 strains of *C. necator* (FIG. 1) harboring pBBR1-ccrSc or pBBR1-ccr$_{Me}$ were cultured in nitrogen-limited, mineral salt medium containing 0.5% fructose as the only carbon source, the accumulated PHA was P(3HB) and 3HHx units were not detected in any of the strains (Table 1).

TABLE 1

Biosynthesis of PHA from Fructose Raw Material by Recombinant *C. necator* Strains Expressing ccr using Vector Derived from pBBR1-MCS2

| Host strain (genotype) | Introduced plasmid | Dry bacterial cell weight (g/L) | PHA accumulation rate (%) | Amount of PHA produced (g/L) | 3HHx fraction (mol %) |
|---|---|---|---|---|---|
| MF01 (phaC$_{MSDG}$-bktB-phaB1) | pBBR1-MCS2 | 2.02 | 52.5 | 1.1 | 0 |
| | pBBR-ccr$_{Me}$ | 1.99 | 53.3 | 1.1 | 0 |
| | pBBR-ccrSc | 1.99 | 53.3 | 1.1 | 0 |
| MF01ΔB1 (phaC$_{MSDG}$-bktB) | pBBR1-MCS2 | 1.63 | 51.9 | 0.84 | 0 |
| | pBBR-ccr$_{Me}$ | 1.06 | 21.5 | 0.23 | 6.7 |
| | pBBR-ccrSc | 1.29 | 33.7 | 0.42 | 2.4 |
| MF01ΔΔB1B3 (phaC$_{MSDG}$-bktB, ΔphaB3) | pBBR1-MCS2 | 0.94 | 11.1 | 0.10 | 0 |
| | pBBR-ccr$_{Me}$ | 0.92 | 7.3 | 0.068 | 19.2 |
| | pBBR-ccrSc | 0.91 | 6.8 | 0.061 | 17.8 |

This result is thought to be due to the pathway for supplying the C4 unit in the form of (R)-3HB-CoA being extremely strong in the host *C. necator* strain MF01, and when strain MF01ΔB1, in which phaB1 had been deleted from the modified pha operon of strain MF01 (FIG. 1), was used as a host, a recombinant strain harboring pBBR1-ccrSc biosynthesized P(3HB-co-3HHx) containing 2.4 mol % of the 3HHx unit at 34% by weight per dry bacterial cell weight from fructose, while a strain harboring pBBR1-ccr$_{Me}$ biosynthesized P(3HB-co-3HHx) containing 6.7 mol % of the 3HHx unit at 22% by weight per dry bacterial cell weight from fructose, thereby suggesting that deficiency of phaB1 is important in P(3HB-co-3HHx) obtained from a saccharide by a strain expressing only ccr.

On the other hand, when culturing *C. necator* strain H16 with fructose, although reduction of acetoacetyl-CoA to (R)-3HB-CoA is mainly due to the function of PhaB1, a paralog thereof in the form of PhaB3 has also been reported to partially function in this manner. Therefore, when strain MB01ΔB1B3, in which phaB3 (present outside the pha operon in a chromosome) was deleted from strain MF01ΔB1 (FIG. 1), was constructed and used as a host strain, P(3HBco-3HHx) was synthesized that contained 18 mol % to 19 mol % of the 3HHx unit although cellular content decreased to about 7% by weight. Although incorporation of the 3HHx unit into PHA was effective for both $ccr_{Sc}$ and $ccr_{Me}$ in strains MF01ΔB1 and strain MF01ΔΔB1B3, strains expressing $ccr_{Me}$ demonstrated higher fractions of 3HHx and lower accumulation of PHA in comparison with strains expressing $ccr_{Sc}$.

In addition, a previously constructed recombinant plasmid pBPP was used as a plasmid having a promoter differing from lac promoter. pBPP is an expression plasmid in which the lac promoter region of pBBR1-MCS2 has been replaced with a phaP1 promoter derived from *C. necator* (Fukui, T., et al., Appl. Microbiol. Biotechnol., 89: 1527-1536 (2011)). An expression vector pBPP-$ccr_{Me}$ (FIG. 2) having $ccr_{Me}$ was constructed and used to transform *C. necator* strain MF01, strain MF01ΔB1 and strain MF01ΔΔB1B3. The resulting recombinant strains were cultured using fructose as the carbon source in the same manner as described above. Only P(3HB) was again biosynthesized in the case of using strain MF01 as the host, whereas P(3HB-co-3HHx) containing 11.1 mol % of the 3HHx unit was biosynthesized at 13% by weight in the case of strain MF01ΔB, and P(3HB-co-3HHx) containing 19.1 mol % of the 3HHx unit was biosynthesized at 4% by weight (Table 2). Incorporation of the 3HHx unit by expression of ccr is accompanied by a decrease in the amount of PHA produced, and pBPP-$ccr_{Me}$ was suggested to exhibit higher $ccr_{Me}$ expression than pBBR1-$ccr_{Me}$ in consideration of the increase in the fraction of 3HHx and the decreased in the PHA production.

TABLE 2

Biosynthesis of PHA from Fructose Raw Material by Recombinant Strains of *C. necator* Expressing ccr using Vector Derived from pBPP

| Host strain | Introduced plasmid | Dry bacterial cell weight (g/L) | PHA accumulation rate (%) | Amount of PHA produced (g/L) | 3HHx fraction (mol %) |
|---|---|---|---|---|---|
| MF01 | pBPP | 1.94 | 54.5 | 1.1 | 0 |
|  | pBPP-$ccr_{Me}$ | 1.77 | 54.3 | 0.90 | 0 |
| MF01ΔB1 | pBPP | 1.69 | 50.8 | 0.86 | 0 |
|  | pBPP-$ccr_{Me}$ | 0.93 | 13.0 | 0.12 | 11.1 |
| MF01ΔΔB1B3 | pBBR1-MCS2 | 0.91 | 9.9 | 0.09 | 0 |
|  | pBBR-$ccr_{Me}$ | 0.98 | 4.4 | 0.043 | 19.1 |

Example 2: Modification of Pathway for Biosynthesis of P(3HB-Co-3HHx) from Saccharide Raw Material The biosynthesis pathway of P(3HB-cc-3HHx) was modified since expression of foreign ccr is accompanied by a decrease in the amount of PHA produced as described above. A gene encoding one of the (R)-specific enoyl-CoA hydratases derived from *C. necator* (phaJ4a) was used for the purpose of enhancing the supply of both (R)-3HB-CoA and (R)-3HHx-CoA. (R)-3HB-CoA and (R)-3HHx-CoA can be formed as a result of the expression product thereof in the form of PhaJ4a catalyzing an (R)-specific hydration reaction on C4 and C6 enoyl-CoAs, although PhaJ4a exhibited a higher level of activity for C6 enoyl-CoA than for C4 enoyl-CoA (International Publication No. WO 2001/105379, Kawashima, Y., et al., Appl. Environ. Microbiol., 78, 493-502 (2012)). An expression vector pBPP-$ccr_{Me}$J4a (FIG. 2) was constructed in which phaJ4a was inserted into pBPP-$ccr_{Me}$ and then used to transform *C. necator* strain MF01, strain MF01ΔB1 and strain MF01ΔΔB1B3. The "phaJ4a" used in the present description corresponds to a gene "phaJ1$_{Cn}$" encoding (R)-specific enoyl-CoA hydratase described in International Publication No. WO 2011/105379.

When the resulting recombinant strains were cultured using fructose as a sole carbon source in the same manner, P(3HB-co-3HHx) containing a trace amount of 3HHx at 0.35 mol % was biosynthesized when strain MF01 was used as the host. In addition, in the case of using strain MF01ΔB1, (3HB-co-3HHx) containing 5.3 mol % of the 3HHx unit was biosynthesized at 31% by weight, while in the case of using strain MF01ΔΔB1B3, P(3HB-co-3HHx) containing 7.2 mol % of the 3HHx unit was biosynthesized at 24% by weight. Although the fraction of 3HHx decreased, the amount of PHA produced increased considerably in comparison with strains harboring pBPP-$ccr_{Me}$ without phaJ4a (Table 3).

TABLE 3

Biosynthesis of PHA from Fructose Raw Material by Recombinant *C. necator* Strains Expressing $ccr_{Me}$ and phaJ4a using Vectors Derived from pBPP

| Host strain | Introduced plasmid | Dry bacterial cell weight (g/L) | PHA accumulation rate (%) | Amount of PHA produced (g/L) | 3HHx fraction (mol %) |
|---|---|---|---|---|---|
| MF01 | bBPP-$ccr_{Me}$J4a | 1.70 | 56.4 | 0.96 | 0.35 |
| MF01ΔB1 | bBPP-$ccr_{Me}$J4a | 1.25 | 31.4 | 0.39 | 5.3 |
| MF01ΔΔB1B3 | bBPP-$ccr_{Me}$J4a | 1.05 | 24.4 | 0.26 | 7.2 |

Figure 3:
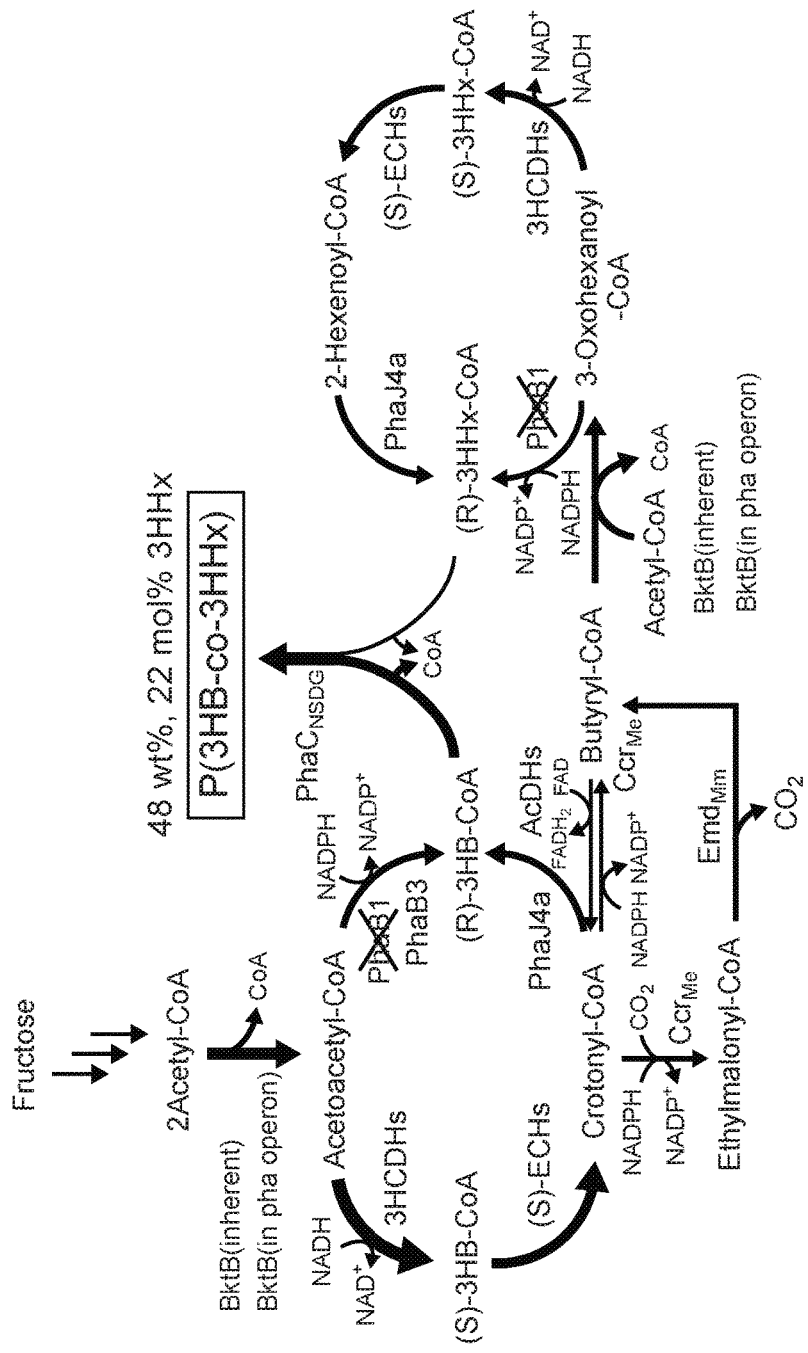
FIG. 3 shows a pathway for biosynthesis of P(3HB-co-3HHx) from fructose in *C. necator* strain MF01ΔB1 having pBPP-ccr$_{Me}$J4a-emd introduced therein.

Crotonyl-CoA reductase has recently been reported to be a bifunctional enzyme that not only exhibits reduction activity to crotonyl-CoA, but also demonstrates reductive carboxylation activity in the presence of carbon dioxide (Erb, T. J., et al., Proc. Natl. Acad. Sci. USA, 106: 8871-8876 (2009)). Although ethylmalonyl-CoA is formed from crotonyl-CoA by this reductive carboxylation reaction, this reaction has the potential to drive alternative pathway that is not desirable in the biosynthesis of P(3HB-co-HHx) of the present invention. On the other hand, an ethylmalonyl-CoA decarboxylase has recently been found for degrading ethylmalonyl-CoA, which is formed in side reactions by enzymes such as propionyl-CoA carboxylase in animals cells, to butyryl-CoA (Linster, C. L., et al., J. Biol. Chem., 286: 42992-43003 (2011)). Therefore, since it was thought that the function of ethylmalonyl-CoA decarboxylase may also be effective in the biosynthesis pathway of P(3HB-co-3HHx) having crotonyl-CoA reductase introduced therein, an expression vector pBPP-$ccr_{Me}$J4a-emd (FIG. 2) was constructed, in which the synthetic gene emd$_{Mm}$ that encodes mouse-derived ethylmalonyl-CoA decarboxylase is additionally inserted into pBPP-$ccr_{Me}$J4a, and then used in the same manner as described above. As a result, in the case of strain MF01ΔB1, P(3HB-co-3HHx) containing 22.2 mol % of the 3HHx unit was biosynthesized from fructose raw material at 48% by weight, while in the case of strain MF01ΔΔB1B3, P(3HB-co-3HHx) containing 37.7 mol % of the 3HHx unit was biosynthesized from fructose raw material at 41% by weight, demonstrating considerable increases in both 3HHx fraction and amount of PHA produced (Table 4, FIG. 3).

In addition, even in strain MF01, P(3HB-co-3HHx) containing 6.4 mol % of the 3HHx unit was produced from fructose at 49% by weight as a result of introducing pBPP-ccr$_{Me}$J4a-emd, demonstrating that co-expression of the genes of crotonyl-CoA reductase, (R)-specific enoyl-CoA hydratase and ethylmalonyl-CoA decarboxylase enabled to produce the copolymer containing significant fraction of the 3HHx unit even in strains not deficient in acetoacetyl-CoA reductase PhaB1.

TABLE 4

Biosynthesis of PHA from Fructose Raw Material by Recombinant *C. necator* Strains Introduced with ccr$_{Me}$, phaJ4a and emd$_{Mm}$ using Vectors Derived from pBPP

| Host strain | Introduced plasmid | Dry bacterial cell weight (g/L) | PHA accumulation rate (%) | Amount of PHA produced (g/L) | 3HHx fraction (mol %) |
|---|---|---|---|---|---|
| MF01 | pBPP-ccr$_{Me}$J4a-emd | 1.76 | 48.5 | 0.85 | 6.4 |
| MF01ΔB1 | pBPP-ccr$_{Me}$J4a-emd | 1.57 | 47.9 | 0.75 | 22.2 |
| MF01ΔΔB1B3 | pBPP-ccr$_{Me}$J4a-emd | 1.42 | 41.1 | 0.59 | 37.7 |

Example 3: Biosynthesis of PHA from Fructose, Glucose and Glycerol by *C. necator* Strain NSDGΔB-GG Although a wild-type strain of *C. necator* in the form of strain H16 grows favorably in fructose or gluconic acid and accumulates polyester, it is unable to grow in glucose and growth is extremely slow when glycerol is used for the carbon source. Glucose is a monosaccharide that composes starch and cellulose, and utilization of glucose is important from the viewpoint of using biomass resources derived from plants. In addition, since glycerol has recently been produced in large volume as a byproduct of the production of biodiesel fuel from vegetable oils, procedures for effective utilization of glycerol is desired.

The present inventors had previously modified *C. necator* strain H16 to impart a high ability to assimilate glucose by introducing a mutation consisting of a single amino acid substitution of the NagE subunit of the putative GlcNAc-specific phosphoenolpyruvate-dependent sugar phosphotransferase system and deleting a gene of putative transcription control factor NagR (Orita, et al., J. Biosci. Bioeng., 113: 63-69 (2012)). In addition, the ability to assimilate glycerol is enhanced by introducing *E. coli*-derived GlpF (glycerol transporter) and GlpK (glycerol kinase) that demonstrate a phosphorylation function following incorporation of glycerol (Fukui, et al., Appl. Microbiol. Biotechnol, 98: 7559-7568 (2014)). Therefore, these two modifications were integrated in *C. necator* strain NSDG, and strain NSDGΔB-GG was produced that is deficient in acetoacetyl-CoA reductase PhaB1. A plasmid pBPP-ccr$_{Me}$-phaJ4a-emd was introduced to establish a pathway for biosynthesizing co-polyester into these strains for the host, and PHA biosynthesis by the resulting recombinant strains was examined on various types of carbon sources.

(i) Construction of *C. necator* Strain NSDGΔB-GG (1) Construction of nagE Mutation and Plasmid Vector for Deleting nagR The ability to assimilate glucose was imparted to *C. necator* strain NSDG by substituting arginine for glycine at position 265 of NagE, and by deleting NagR. The amino acid substitution of NagE was introduced by a mutation that substitutes cytosine for guanine at the 793rd base of nagE gene in a chromosome. The homologous recombination plasmid pK18msNagE_G265R used for this purpose was constructed in the manner indicated below. First, a region containing nagE along with the flanking upstream and downstream regions of approximately 1 kbp therefrom was amplified by PCR using genomic DNA of *C. necator* strain H16 as a template and using the oligonucleotides of Sequence 15 and Sequence 16 indicated below as primers.

Sequence 15:
(SEQ ID NO: 19)
GGAATTCTATTGAGGTGGCCGCGAATATCGGCAGCCT

Sequence 16:
(SEQ ID NO: 20)
GGAATTCAGGTGCGCTTCGACAAGTCATACTTT

The 5'-end of the amplified fragment was phosphorylated and inserted into the HincII site of general-purpose plasmid pUC118. A mutation was then introduced that substitutes cytosine for guanine of the 793rd base of nagE gene by inverse PCR using this plasmid as a template and using the oligonucleotides of Sequence 17 and Sequence 18 indicated below as primers.

Sequence 17:
(SEQ ID NO: 21)
GGCCAACCAGCGCGCGCCCCGCCGGCGGCGTCTCGT

Sequence 18:
(SEQ ID NO: 22)
GCATGCTGTTCTCGATGGCACTGACCT

The 5'-end of the amplified fragment was phosphorylated and self-ligated. The resulting plasmid was treated with restriction enzymes BamHI and XbaI to obtain a fragment containing the mutant nagE gene. This fragment was then ligated with a fragment of pK18mobSacB cleaved with the same restriction enzymes BamHI and XbaI to obtain pK18msNagE_G265R.

A homologous recombination plasmid pK18msΔnagR for deleting nagR gene in a chromosome of *C. necator* strain NSDG was produced in the manner indicated below. First, a region containing nagR along with the flanking upstream and downstream regions of approximately 1 kbp therefrom was amplified by PCR using genomic DNA of *C. necator* strain H16 as a template and using the oligonucleotides of Sequence 19 and Sequence 20 indicated below as primers.

Sequence 19:
(SEQ ID NO: 23)
TGCAGTTCGTATGCGACCGCATCGA

Sequence 20:
(SEQ ID NO: 24)
GGAATTCAGGTGCGCTTCGACAAGTCATACTTT

The 5'-end of the amplified fragment was phosphorylated and inserted into the HincII site of general-purpose plasmid pUC118. A fragment of plasmid-backbone flaking with the upstream and downstream region of nagR, not containing nagR gene, was then amplified by inverse PCR using this plasmid as a template and using the oligonucleotides of Sequence 21 and Sequence 22 indicated below as primers.

Sequence 21:
(SEQ ID NO: 25)
TGCCCGGCACGCCCGGCAACCGGCGGCTCGA

Sequence 22:
(SEQ ID NO: 26)
TGCGAATCCTCGTAGGTACCAGAGTGTGGA

The 5'-end of the amplified fragment was phosphorylated and self-ligated. The resulting plasmid was treated with restriction enzymes EcoRI and HindIII to obtain a fragment in which the upstream and downstream regions of nagR had been connected without nagR. This fragment was then ligated with a fragment of pK18mobSacB cleaved with the same restriction enzymes EcoRI and HindIII to obtain pK18msΔnagR.

(2) Construction of Plasmid Vector for Introducing E. coli-Derived E. coli Derived glpFK The ability of C. necator strain NSDG to assimilate glycerol was enhanced by inserting E. coli-derived glpF-glpK gene (to be referred to as glpFK) at upstream of a gene h16_A2858 having an unknown function in a chromosome of C. necator strain NSDG. A homologous recombination plasmid pK18msglpFK-A2858 was constructed for this purpose in the manner indicated below. First, a fragment containing upstream and downstream regions of approximately 750 bp from the start codon of h16_A2858 gene was amplified by PCR using genomic DNA of C. necator strain H16 as a template and using the oligonucleotides of Sequence 23 and Sequence 24 indicated below as primers.

Sequence 23:
(SEQ ID NO: 27)
ATACCGTCGACGGTGCTGGCTCCGGAAGGTTT

Sequence 24:
(SEQ ID NO: 28)
CTGCAGTCGACCCTGCGCGCCCACGCCGCTTT

The amplified fragment was treated with restriction enzyme SalI and inserted into pK18mobSacB at the same SalI site. A fragment that was ring-opened at the start codon of h16_A2858 gene was amplified by inverse PCR using the resulting plasmid as a template and using the oligonucleotides of Sequence 25 and Sequence 26 indicated below as primers.

Sequence 25:
(SEQ ID NO: 29)
GCGGGCAACGGATGGAGGTAAGCA

Sequence 26:
(SEQ ID NO. 30)
CTTACCTCCATCCGTTGCCCGCTTCG

On the other hand, a region of glpFK genes was amplified by PCR using genomic DNA of E. coli strain MG1655 as a template and using the oligonucleotides of Sequence 27 and Sequence 28 indicated below as primers.

Sequence 27:
(SEQ ID NO: 31)
ATGAGTCAAACATCAACCTT

Sequence 28:
(SEQ ID NO: 32)
TTATTCGTCGTGTTCTTCCCAC

The 5'-end of the amplified fragment of the glpFK region was phosphorylated and ligated with the aforementioned linear fragment formed after the ring-opening at the start codon of h16_A2858 gene by inverse PCR. The plasmid in which glpFK gene was inserted into upstream of the h16_A2858 gene in the same orientation as h16_A2858 gene was selected by PCR to obtain pK18msglpFK-A2858.

(3) Construction of Plasmid Vector for Deleting PhaB1

A plasmid pK18msAR2 for deleting phaB1 gene that encodes acetoacetyl-CoA reductase PhaB1 from the pha operon in a chromosome of C. necator strain NSDG was constructed in the manner indicated below based on a previously constructed pK18msNSDG-AB (International Publication No. WO 2011/105379). First, a region of approximately 1 kbp downstream from phaB1 gene was amplified by PCR using genomic DNA of C. necator strain H16 as a template and using the oligonucleotides of Sequence 29 and Sequence 30 indicated below as primers.

Sequence 29:
(SEQ ID NO: 33)
TCGACCGGCGCCGACTTCTC

Sequence 30:
(SEQ ID NO: 34)
GCATGCCAGTGTCTTACTTCT

The amplified fragment was treated with restriction enzymes NdeI and SphI, and ligated with a fragment of pK18msNSDG-AB treated with the same restriction enzymes NdeI and SphI to obtain pK18msC'R. In addition, a region of β-ketothiolase gene phaA, having NdeI restriction sites at both ends thereof was amplified by PCR using genomic DNA of C. necator strain H16 as a template and using the oligonucleotides of Sequence 31 and Sequence 32 indicate below as primers.

Sequence 31:
(SEQ ID NO: 35)
CGCCGCATGACGCTTGCATA

Sequence 32:
(SEQ ID NO: 36)
CCATATGCGGCCCCGGAAAACCCC

The amplified fragment was treated with restriction enzyme NdeI and ligated with a fragment of pK18msC'R cleaved with the same restriction enzyme NdeRI to obtain pK18msC'AR. The phaC$_{NSDG}$ gene therein was removed by digesting this plasmid with restriction enzymes SbfI and BamHI followed by blunting the ends and self-ligating to obtain pK18msAR2.

(4) Transformation of *C. necator* by Conjugal Transfer and Homologous Recombination Introduction of a homologous recombination vectors based on pK18mobSacB constructed in the manner described above into *C. necator* and selection of the homologous recombinant strain were carried out using the same methods as Example 1. *C. necator* strain NSDGΔB-GG imparted with the ability to assimilate glucose, enhanced ability to assimilate glycerol, and deficient in PhaB1 was constructed by sequential homologous recombination using pK18msNagE_G265R, pK18msΔnagR and pK18msglpFK-A2858, pK18msAR2 introduced by conjugal transfer, followed by appropriate selections. Moreover, plasmid pBPP-ccr$_{Me}$-phaJ4a-emd$_{Mm}$ for establishing the pathway for biosynthesizing P(3HB-cc-3HHx) was introduced into the resulting strain NSDGΔB-GG by conjugal transfer.

(5) Biosynthesis of PHA from Glucose, Fructose and Glycerol Raw Materials

Biosynthesis of PHA by the constructed recombinant strains was carried out by culturing in nitrogen-limited, mineral salt medium containing fructose, glucose or glycerol at 1.0% by weight as the sole carbon source. Cultivation time was set for 72 hours in the cases of fructose and glucose and 96 hours in the case of glycerol. The cellular content and composition of the PHA that accumulated within the bacterial cells were determined by gas chromatography.

TABLE 5

Biosynthesis of PHA from Fructose, Glucose and Glycerol by *C. necator* Strain NSDGΔB-GG Introduced with pBPP-ccr$_{Me}$-phaJ4a-emd$_{Mm}$

| Host strain | Introduced plasmid | Carbon source | Dry bacterial cell weight (g/L) | PHA accumulation rate (%) | Amount of PHA produced (g/L) | 3HHx fraction (mol %) |
| --- | --- | --- | --- | --- | --- | --- |
| NSDGΔB-GG | pBPP-ccr$_{Me}$J4a-emd | Fructose | 3.29 | 71.0 | 2.34 | 23.9 |
|  |  | Glucose | 2.90 | 67.5 | 1.96 | 21.8 |
|  |  | Glycerol | 1.23 | 29.4 | 0.36 | 13.1 |

The results of culturing *C. necator* strain NSDGΔB-GG harboring pBPP-ccr$_{Me}$J4a-emd are shown in Table 5. When the fructose concentration was set to 1% by weight, P(3HB-co-3HHx) having a high fraction of 3HHx (24 mol %) was efficiently biosynthesized that demonstrated an accumulation of 71% by weight, corresponding to production of 2.34 g-PHA/L. In the case of glucose, although the amount produced was somewhat lower than fructose at the same concentration, P(3HB-co-3HHx) having a 3HHx fraction of 22 mol % was biosynthesized with 1.96 g/L. In the case of using glycerol for the carbon source, although the amount of PHA produced significantly decreased to 0.36 g/L, P(3HB-co-3HHx) composed of 13.1 mol % 3HHx fraction was biosynthesized. Namely, production of the co-polyester was also possible using glucose and glycerol as raw materials. The results in the present invention demonstrated the potential of the artificial P(3HB-co-3HHx) biosynthesis pathway for efficient production of the copolyester from a diverse range of raw materials by introducing into host microorganisms capable of assimilating raw materials desired to be utilized.

INDUSTRIAL APPLICABILITY

A method can be provided for producing P(3HB-co-3HHx) having a high fraction of 3HHx at a high cellular content using saccharides or glycerol as starting raw materials by constructing a novel metabolic pathway for the formation of a 3HB unit and 3HHx unit from acetyl-CoA by genetically modified *C. necator*.

All publications and patent documents cited in the present description are incorporated in the present description in their entirety by reference. Furthermore, although specific embodiments of the present invention have been explained in the present description for the purpose of exemplification, it can be easily understood by a person with ordinary skill in the art that the present invention may be subjected to various modifications provided they do not deviate from the spirit and scope of the present invention.

The invention claimed is:

1. A method for producing poly(3-hydroxybutyrate-co-3-hydroxyhexanote), comprising: transforming a recombinant *Cupriavidus necator* strain imparted with the ability to produce poly(3-hydroxybutyrate-co-3-hydroxyhexanoate) by homologous recombination of crotonyl-CoA reductase gene, (R)-specific enoyl-CoA hydratase gene and ethylmalonyl-CoA decarboxylase gene in a chromosome of the strain, or transforming by introducing an autonomously replicating vector having these genes incorporated in that strain, and cultivating the transformant in a medium containing a saccharide and/or glycerol as a carbon source, wherein the crotonyl-CoA reductase gene is composed of:
 (a) a nucleic acid containing the base sequence set forth in SEQ ID NO: 1 or 2, or
 (b) a nucleic acid that hybridizes under stringent conditions with a nucleic acid containing the base sequence set forth in SEQ ID NO: 1 or 2 and encodes a protein having catalytic activity that forms butyryl-CoA from crotonyl-CoA, wherein the (R)-specific enoyl-CoA hydratase gene is obtained from *Cupriavidus necator*, and is composed of:
 (a) a nucleic acid containing the base sequence set forth in SEQ ID NO: 3, or
 (b) a nucleic acid that hybridizes under stringent conditions with a nucleic acid containing the base sequence set forth in SEQ ID NO: 3 and encodes a protein having activity that converts an intermediate in the fatty acid β-oxidation pathway in the form of 2-enoyl-CoA to (R)-3-hydroxyacyl-CoA, and wherein the ethylmalonyl-CoA decarboxylase gene is composed of:
 (a) a nucleic acid containing the base sequence set forth in SEQ ID NO: 4, or
 (b) a nucleic acid that hybridizes under stringent conditions with a nucleic acid containing the base sequence set forth in SEQ ID NO: 4 and encodes a protein having catalytic activity that forms butyryl-CoA by decarboxylation of ethylmalonyl-CoA, wherein the stringent conditions comprise prewashing in a prewashing solution containing 5×SSC, 0.5% SDS and 1.0 mM EDTA (pH 8.0), hybridizing in a hybridization solution containing 2×SSC to 6×SSC and approximately 50% formamide at about 40° C. to 50° C., and washing in 0.5×SSC and 0.1% SDS at about 60° C.

2. The method according to claim 1, wherein the *Cupriavidus necator* is strain JMP134 (DSM4058) or strain H16 (DSM428).